(12) United States Patent
Montagu

(10) Patent No.: US 6,407,858 B1
(45) Date of Patent: Jun. 18, 2002

(54) FOCUSING OF MICROSCOPES AND READING OF MICROARRAYS

(75) Inventor: Jean I. Montagu, Brookline, MA (US)

(73) Assignee: Genetic Microsystems, INC, Woburn, MA (US)

( * ) Notice: Subject to any disclaimer, the term of this patent is extended or adjusted under 35 U.S.C. 154(b) by 0 days.

(21) Appl. No.: 09/500,548

(22) Filed: Feb. 9, 2000

Related U.S. Application Data

(63) Continuation of application No. 09/122,216, filed on Jul. 24, 1998, and a continuation-in-part of application No. 09/079,790, filed on May 15, 1998, now Pat. No. 6,262,838, and a continuation-in-part of application No. 09/079,324, filed on May 14, 1998, now Pat. No. 6,269,846.
(60) Provisional application No. 60/183,021, filed on May 14, 1998.

(51) Int. Cl.[7] ............................................. G02B 21/26

(52) U.S. Cl. ..................... 359/391; 359/393; 359/394; 359/368; 250/201.3

(58) Field of Search ................................. 359/368, 381, 359/391, 393, 394; 250/548, 201.3, 201.4

(56) References Cited

U.S. PATENT DOCUMENTS

| | | | |
|---|---|---|---|
| 2,868,020 A | 1/1959 | Williams, Jr. ................ | 73/432 |
| 3,329,964 A | 7/1967 | Mutschler et al. ............ | 346/78 |
| 3,334,354 A | 8/1967 | Mutschler .................... | 346/140 |

(List continued on next page.)

FOREIGN PATENT DOCUMENTS

| | | |
|---|---|---|
| EP | 0 373 203 | 6/1990 |
| WO | WO 95/04594 | 2/1995 |
| WO | WO 95/09248 | 4/1995 |

OTHER PUBLICATIONS

Castellino, Alexander M.; "When the Chips are Down"; *Genome Research*; vol. 7, No. 10; (1997), pp 943–946.

(List continued on next page.)

*Primary Examiner*—Cassandra Spyrou
*Assistant Examiner*—Leo Boutsikaris
(74) *Attorney, Agent, or Firm*—Ivan D. Zitkovsky; Alan B. Sherr; Philip L. McGarrigle

(57) ABSTRACT

Microscopes, including viewing and other microscopic systems, employ a hinged, tiltable plate to adjust focus on a flat object such as a microscope slide or biochip by motion, achieved by tilting, which is substantially normal to the focus point on the plane of the object. By employing two such tiltable arrangements, relatively long scan lines of e.g., flying objective, single pixel on-axis scanning can be accommodated. The tilting support plate is specifically constructed to provide tailored locations for different objects in series along the Y axis of the plate. The plate can accommodate heaters and cooled plates and/or the flat object being examined. In a fluorescence scanning microscope, locations are specifically adapted to receive microscope slides and biochip cartridges such as Affymetrix's "Gene Chip®". A scanning microscope under computer control, employing such a focusing action, enables unattended scanning of biochips with a simple and economical instrument. Also shown are flexure-mounting of a support plate to define the hinge axis, techniques for automatically determining position and focus, and a rotatably oscillating flying microobjective scanner combined with the tilting plane focus system. Construction and control techniques are shown that realize simple and accurate focusing. Methods of examination of biological materials are disclosed. Simple and efficient focused scanning with a flying micro-objective of ordered arrays of nucleotides and nucleic acid fragments carried upon a microscope slide or other substrate is disclosed. Quantified fluorescence imaging is economically achieved by combined use of the described scanning and focusing arrangement and use of simple and accurate calibration modules respectively for example for Affymetrix's "Gene Chip" microarray modules and for microscope slides.

41 Claims, 20 Drawing Sheets

U.S. PATENT DOCUMENTS

| | | | |
|---|---|---|---|
| 3,407,018 A | * 10/1968 | Miller | 359/896 |
| 3,568,735 A | 3/1971 | Lancaster | 141/238 |
| 3,826,558 A | * 7/1974 | Rasberry | 359/394 |
| 4,041,995 A | 8/1977 | Columbus | 141/275 |
| 4,096,825 A | 6/1978 | Golias et al. | 118/221 |
| 4,142,656 A | 3/1979 | Smith et al. | 222/325 |
| 4,322,063 A | 3/1982 | Fishbeck et al. | 267/160 |
| 4,340,390 A | 7/1982 | Collins et al. | 23/230 |
| 4,387,384 A | 6/1983 | Sue | 346/140 |
| 4,434,672 A | 3/1984 | Williamson et al. | 73/864.22 |
| 4,441,532 A | 4/1984 | Hrubesh | 141/1 |
| 4,452,899 A | 6/1984 | Alston | 436/46 |
| 4,565,094 A | * 1/1986 | Sedgewick | 73/432 |
| 4,567,585 A | 1/1986 | Gelbart | 369/97 |
| 4,627,009 A | 12/1986 | Holmes et al. | 364/559 |
| 4,635,488 A | 1/1987 | Kremer | 73/864.22 |
| 4,656,007 A | 4/1987 | Douchy et al. | 422/64 |
| 4,659,677 A | 4/1987 | Glover et al. | 436/174 |
| 4,688,908 A | 8/1987 | Moore | 359/393 |
| 4,737,344 A | 4/1988 | Koizumi et al. | 422/100 |
| 4,832,474 A | 5/1989 | Yohinaga et al. | 359/393 |
| 4,891,526 A | 1/1990 | Reeds | 250/442.1 |
| 4,981,783 A | 1/1991 | Augenlicht | 435/6 |
| 5,051,594 A | * 9/1991 | Tsuda et al. | 250/442.11 |
| 5,202,231 A | 4/1993 | Drmanac | 422/100 |
| 5,204,268 A | 4/1993 | Matsumoto | 436/44 |
| 5,213,764 A | 5/1993 | Kerr et al. | 422/100 |
| 5,223,225 A | 6/1993 | Gautsch | 422/100 |
| 5,224,088 A | * 6/1993 | Atiya | 369/97 |
| 5,262,128 A | 11/1993 | Leighton et al. | 422/100 |
| 5,306,510 A | 4/1994 | Meltzer | 422/65 |
| 5,323,712 A | * 6/1994 | Kikuiri | 359/393 |
| 5,337,178 A | 8/1994 | Kung et al. | 359/393 |
| 5,338,688 A | 8/1994 | Deeg et al. | 436/180 |
| 5,344,666 A | 9/1994 | Levine | 427/2.11 |
| 5,351,925 A | 10/1994 | Druais | 248/325 |
| 5,428,690 A | 6/1995 | Bacus et al. | 382/128 |
| 5,436,129 A | 7/1995 | Stapleton | 435/6 |
| 5,443,791 A | 8/1995 | Cathcart et al. | 422/65 |
| 5,461,237 A | 10/1995 | Wakamoto et al. | 250/548 |
| 5,492,806 A | 2/1996 | Drmanac et al. | 435/5 |
| 5,525,464 A | 6/1996 | Drmanac et al. | 435/6 |
| 5,540,891 A | 7/1996 | Portmann et al. | 422/102 |
| 5,551,487 A | 9/1996 | Gordon et al. | 141/1 |
| 5,583,691 A | 12/1996 | Yamane et al. | 359/393 |
| 5,607,861 A | 3/1997 | Komatsu et al. | 436/50 |
| 5,626,740 A | 5/1997 | Seto et al. | 205/789 |
| 5,665,312 A | 9/1997 | Sperber et al. | 422/81 |
| 5,700,637 A | 12/1997 | Southern et al. | |
| 5,756,050 A | 5/1998 | Ershow et al. | 422/100 |
| 5,770,151 A | 6/1998 | Roach et al. | 422/63 |
| 5,800,992 A | 9/1998 | Fodor et al. | 435/6 |
| 5,807,522 A | 9/1998 | Brown et al. | 422/50 |
| 5,882,930 A | 3/1999 | Baier | 436/49 |
| 5,895,630 A | 4/1999 | Skaborn et al. | 422/100 |

OTHER PUBLICATIONS

Ekins, R.P., et al.; "Multianalyte Immunoassay: The Immunological 'Compact Disk' of the Future"; *Journal of Clinical Immunoassay*; vol. 13, No. 4; (1990), pp 169–181.

NORMAG, Northern Magnetics Inc., company brochure.

NORMAG, "Single Axis High Performance Linear Stepper Motors", product description, pp 1.

"The Perfect Solution for Your Testing Problem", © Ostby Barton, (1997); product description, pp 1.

BioRobotics, "The MicroGrid", product description, pp 2.

"Gridding & Replicating Application", Revised: Nov. 1997 © *PBA Technology Ltd.*, pp 1–2.

Geysen, H. M., et al.; "Strategies for epitope analysis using peptide synthesis"; *Journal of Immunological Methods*; vol. 102; (1987), pp 259–274.

Graves, David J., et al.; "System for Preparing Microhybridization Arrays on Glass Slides"; *Analytical Chemistry*; vol. 70, (1998) pp 5085–5092.

Kalachikov, S., et al.; Colony Selection with an Automated 383–Pin High–Density Replicating Tool (HDRT); BioRobotics, ©1996 Beckman Instruments, Inc.; pp 1–7.

Lemieux, B., et al.; "Overview of DNA chip technology"; *Molecular Breeding*; vol. 4, (1998); pp 277–289.

Pease et al.; "Light–generated oligonucleotide arrays for rapid DNA sequence analysis"; *Proc. Natl. Acad. Sci. USA*; vol. 91, pp. 5022–5026, May 1994.

Southern et al.; "Molecular interactions on microarrays"; The Chipping Forecast; *Nature Genetics*; vol. 21, pp. 5–9; Jan. 1999.

Trent et al., "Workshop on Methods and Applications of DNA Microarray Technology"; Jan. 11–13, 1998.

"Microfiltration Apparatus"; *Chromatography Electorphoresis Immunochemistry Molecular Biology HPLC*; catalogue M 1987.

Hames et al.; "Nucleic Acid Hybridization: A Practical Approach"; *IRL Press* Oxford England; 1985.

"BioRobotics Latest Developments"; BioRobotics, Beckman Instruments, Inc.; 1997.

Abstracts of papers presented at the 1994 meeting on Genome Mapping & Sequencing; pp. 48, 60–62, 198, 203, 296–297; May 11–15, 1994.

Gilson; "Raising The Speed Limit On Liquid Handling . . . Again!" advertisement p 1.

* cited by examiner

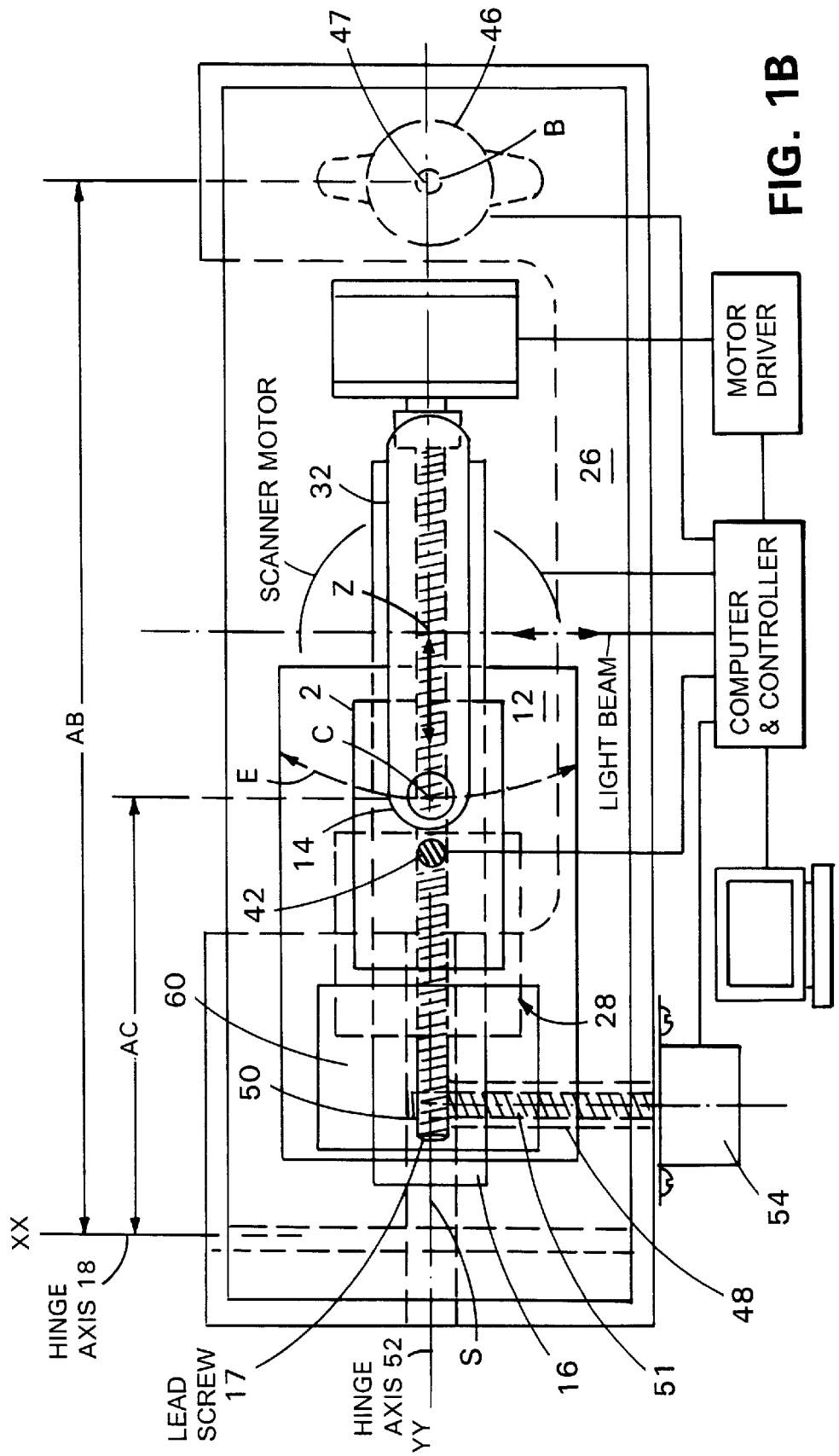

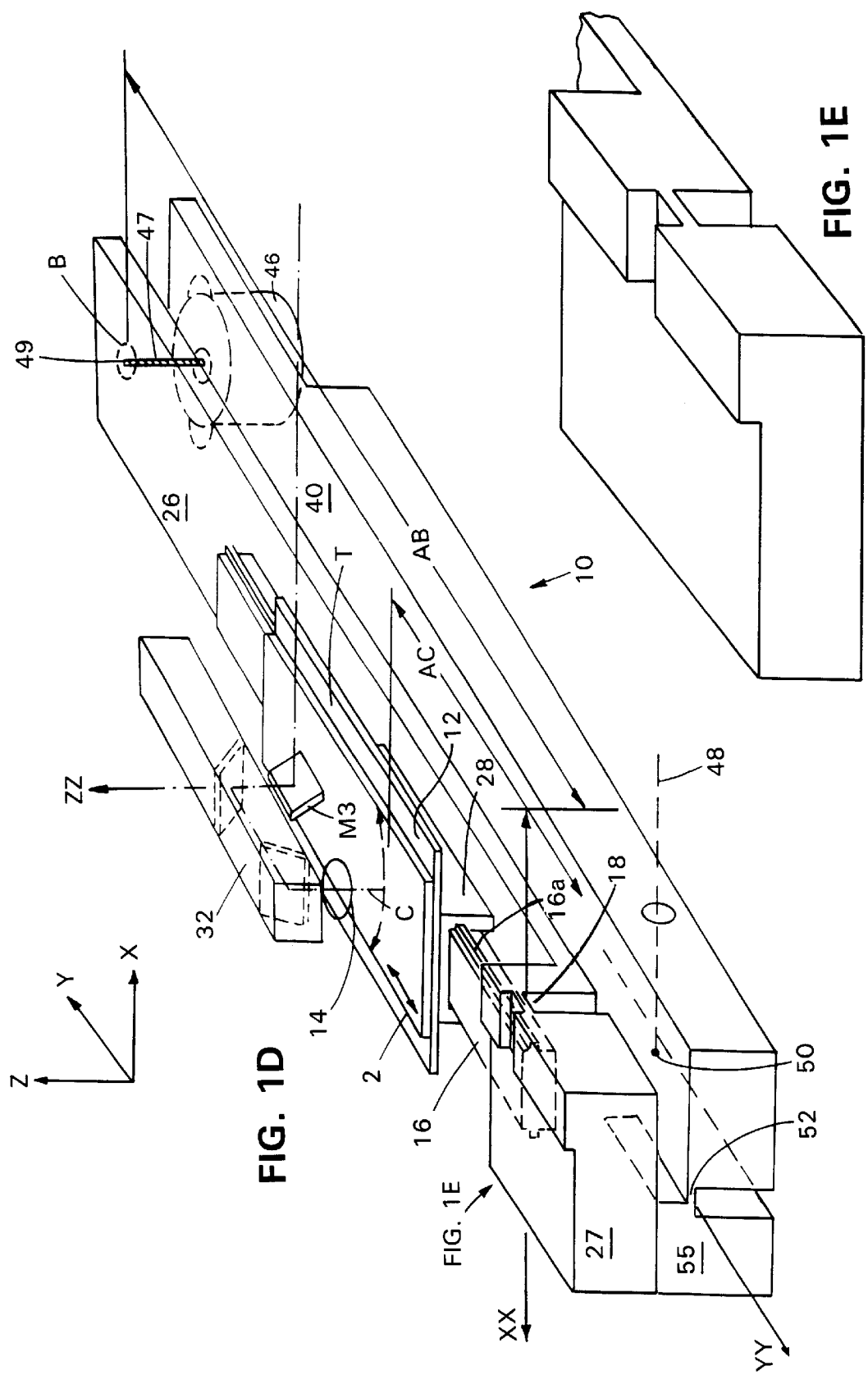

MAGNIFIED CROSS SECTION OF ALIGNMENT TOOL

ALIGNMENT TOOL PLAN VIEW

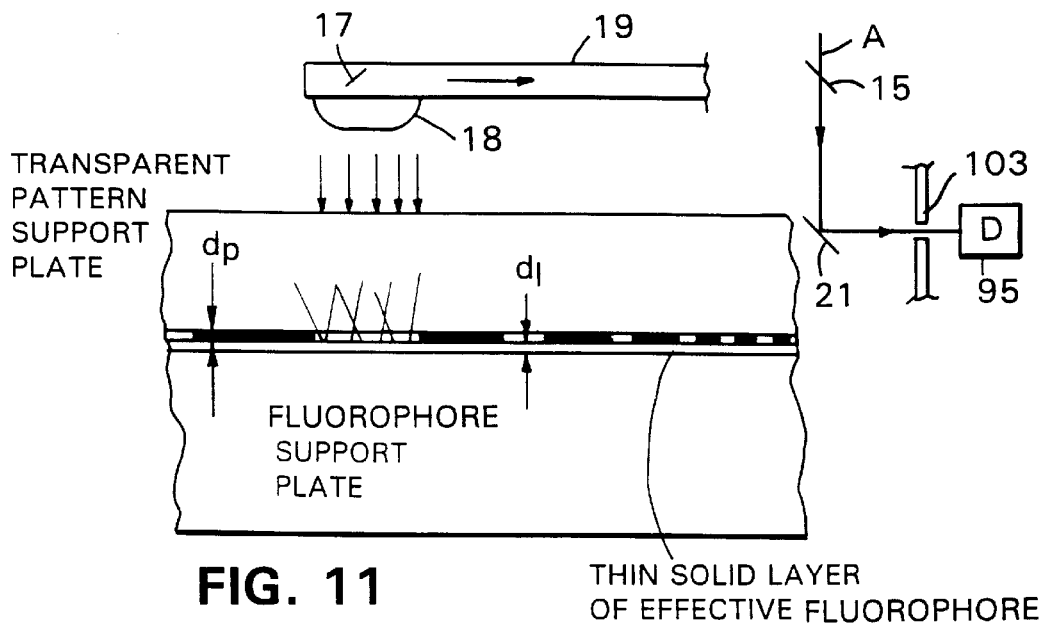
FIG. 11
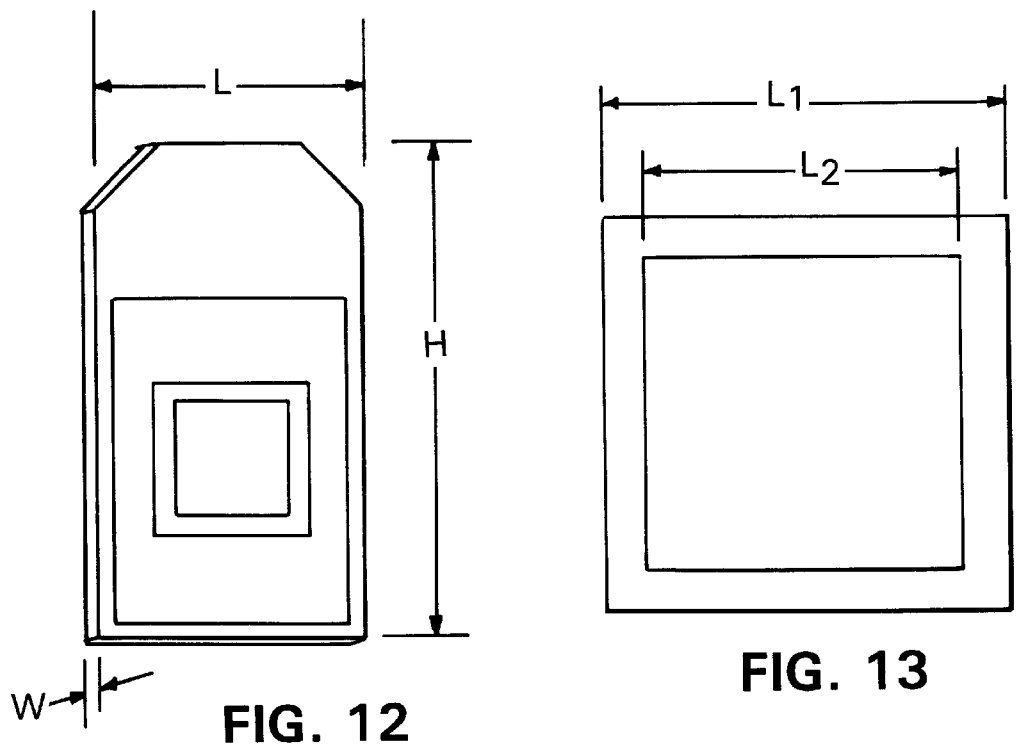
FIG. 12
FIG. 13

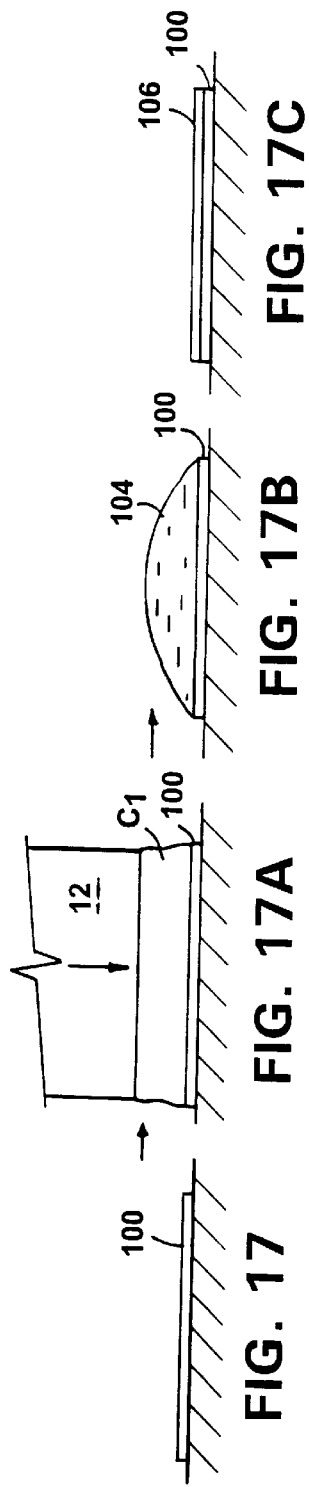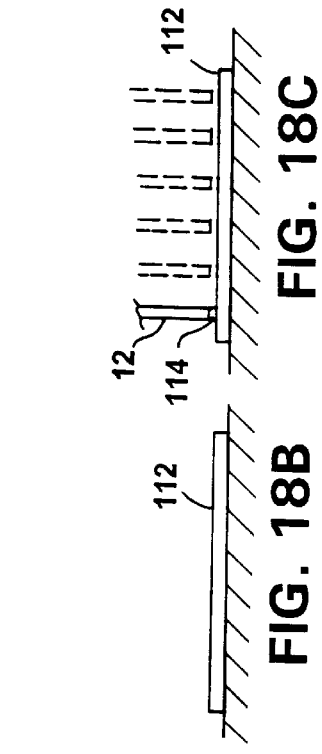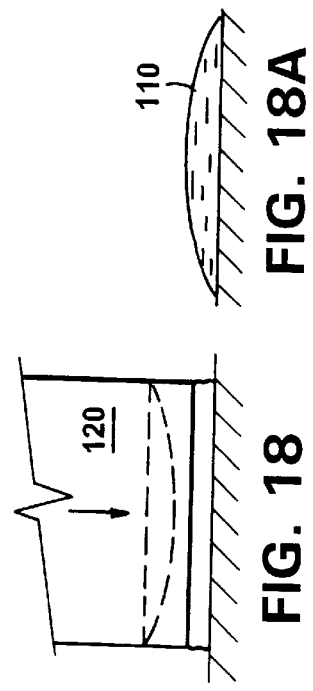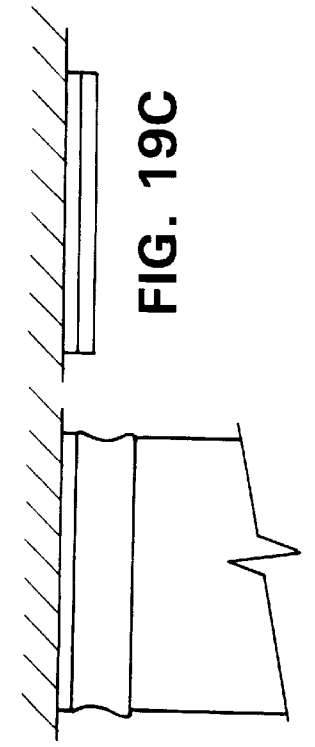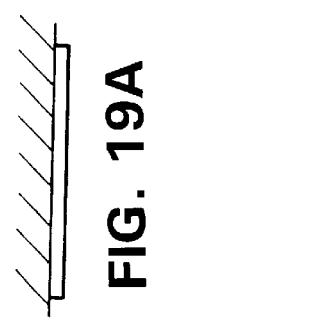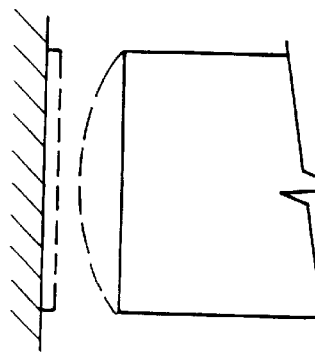

FOCUSING OF MICROSCOPES AND READING OF MICROARRAYS

CROSS REFERENCE TO RELATED APPLICATIONS

This application is a continuation-in-part of U.S. Ser. No. 09/079,790, filed May 15, 1998, entitled "Focusing Microscope Systems" now U.S. Pat. No. 6,262,838; of U.S. Ser. No. 09/079,324, filed May 14, 1998, now U.S. Pat. No. 0,269,846 entitled "Depositing Fluid Specimens On Substrates, Resulting Ordered Arrays, Techniques For Analysis Of Deposited Arrays"; and a continuation U.S. Ser. No. 09/122,216, filed Jul. 24, 1998, entitled "Depositing Fluid Specimens On Substrates, Resulting Ordered Arrays, Techniques For Deposition Of Arrays" now U.S. Pat. No. 6,269,846 all of which are hereby incorporated by reference. This application also claims priority from PCT Application PCT/US99/00730 (WO99/3670), Entitled "Depositing Fluid Specimens On Substrates, Resulting Ordered Arrays, Techniques For Analysis Of Deposited Arrays" incorporated by reference.

This application is also related to U.S. application Ser. No. 09/045,547, filed Mar. 20, 1998, entitled "Wide Field of View and High Speed Scanning Microscopy," now U.S. Pat. No. 6,201,639, U.S. application Ser. No. 09/170,847, filed Oct. 13, 1998, entitled "Wide Field of View and High Speed Scanning Microscopy" and PCT Application PCT/US99/06097 (WO99/47694), entitled "Wide Field Of View And High Speed Scanning Microscopy" all of which are hereby incorporated by reference.

BACKGROUND OF THE INVENTION

Focusing mechanisms for microscopes are employed to position the object at the plane of focus of the instrument, to enable the object to be examined, i.e. inspected, illuminated or otherwise acted upon. Typically the object is placed upon a platform that moves laterally relative to the optical axis of the objective, to bring the area of interest of the object into alignment with the optical axis. The platform is then raised or lowered (translated) along the optical axis to achieve best focus. If it is necessary to register the optical axis with regions of the object larger than the field of view of the objective lens, the platform and object are further moved laterally in a sequence of steps to view the entire area. In some cases, microscopes are constructed to translate the objective lens or the entire microscope along the optical axis to reach best focus and in some cases the objective lens is moved laterally to bring the optical axis and areas of interest into alignment.

A known technique for translating the platform and object in the direction of the optical axis employs a precision dovetail mechanism that is activated by a manual rack and pinion or a motorized lead screw. In many cases this mechanism must be constructed with high accuracy to be capable of micron or sub-micron positional resolution, which results in high cost.

In the case of wide field of view microscopes in which lateral motion of the object or microscope objective is required, such as flying objective scanners, there is need for reliable, low cost and fast focus mechanisms of high accuracy. This need exists particularly in respect of investigational tools for biology, e.g., for viewing arrays of fluorescently labeled microorganisms and DNA assays as well as for viewing entire biopsy samples, which may be as large as a square centimeter or larger. ("DNA" is used here to designate the full range of nucleic acids of interest to the field of biotechnology.) In particular low cost reading of biochips such as the "Gene Chip®" by Affymetrix Inc., and of high density spotted micro arrays or microscope slides is a widely felt need.

According to present biological analytical technology, arrays of fluorescently labeled microorganisms and DNA assays are created in two dimensional fields. The objects to be examined in an array are, for example, DNA fragments that have discriminating sequence information. Biological laboratories have targeted round or square objects for the arrays (e.g., spots of DNA) of diameters or side dimensions of the order of 20 to 250 micron, the spot size depending primarily upon the total number of objects to be represented in the array.

DNA arrays are typically probed with fluorescently labeled fragments of potentially complementary strands. When a match occurs between a fragment in a deposited spot and a fluorescently labeled fragment probe, hybridization occurs, and a positive "score" can be recorded under fluoroscopic examination. Because fluorescence, whether natural or stimulated by illumination, is a weak signal, a "score" is identified for a DNA spot by the intensity of the fluorescence from the spot compared to reading(s) for the background that directly surrounds the specific spot. By controlled deposition of spots of a variety of DNA fragments in the array and by observing the matches or "scores" that occur at known spot addresses, important information concerning nucleic acids can be inferred. For this technology to expand widely, economical instruments are required that can rapidly and accurately scan the fluorescently labeled objects over a wide field of view, e.g. a field of view that is approximately 22 mm wide, the useful width of conventional glass microscope slides.

The large volume of data to be evaluated also calls for unattended operation of such instruments upon a sequence of slides or biochips, including automatic focusing of the microscope for each slide, biochip, or other object and in some cases, automatic focusing as scanning of a particular object proceeds.

Microscopes or microscope-like instruments have been developed to inspect, illuminate or otherwise treat wide areas, based on scanning principles. In the case of inspection, the image is constructed electronically from a succession of acquired single picture elements during relative scanning movement between the object and the microscope. Focusing in these instruments is commonly automated, but there are significant economic and operational drawbacks in the systems that have been commercially available.

For a number of reasons, proper focusing is a critical need for automated microscopes where the material to be investigated is disposed over a wide area of a microscope slide or located on a window of a biochip holder. A microscope slide is typically a slab of float glass approximately 25×75 mm in x, y dimensions and about 1+0.1/−0.2 mm thick as defined by industrial standard ISO 8037-1-1986E. It is common for microscope slides to be slightly bowed, as they are not very rigid and can be deformed when clamped. In the normal installation of a slide in a microscope, the slide is caused to rest upon a flat surface and is held in place by gently pushing its edges against stops, a technique which alleviates most deformation. Other types of substrates for microscopic examination, including arrays provided on relatively thin glass cover slips and on plastic substrates or holders, likewise have variation in thickness or shape and are subject to deformation or the area to be viewed does not have an accurate or reliable reference location.

The depth of field (focus tolerance) and the resolution of a given microscope are inter-related, being defined by the laws of physics. The better the resolution, the smaller is the depth of focus. Present day biochip examination calls for pixel resolution between 2 and 10 micron which corresponds to a depth of field between approximately 4 and 200 micron, the particular values depending upon the optical configuration and the application. For pathology, the pixel may have 0.5 micron diameter and the depth of field 2 micron. Since the thickness variation of commercial microscope slides is greater than such values, when the slide rests upon its back surface, repeated focusing of the microscope is compulsory and autofocusing is generally desirable.

In cases where slides or other objects are sufficiently uniform for the purpose at hand, focus is obtained once per slide or object to be microscopically examined, during a setup procedure.

In some cases, automated microscopes employ dynamic focusing features, i.e. features enabling continual adjustment of focus as scanning of a given slide or object proceeds. For this purpose an algorithm is employed to define focus. Commonly, dynamic systems analyze the image acquired through the optical path of the instrument. In response to these readings, the algorithm is employed under computer control, to cause an element of the system to be raised and lowered as scanning proceeds, to translate the object along the optical axis to achieve focus in a dynamic manner. Frequently the pattern of raising and lowering is based upon a prescan of the overall object, from which positional information has been stored for use to control focus during the following examination scan. Typically instruments that enable dynamic focus adjustment with great precision require great cost.

A common attempt to avoid the cost and delays of prior art auto-focus techniques has been to incorporate a mechanism that forces a microscope slide against three buttresses, in an attempt to achieve precise location of the slide. Unfortunately, such techniques have unsatisfactory aspects, in causing the slide to deform, especially with bowing. This frequently results in loss of resolution. Also, such technique can only be used when the surface to be inspected is rigid and co-planar with the buttress reference location.

SUMMARY OF THE INVENTION

The present invention provides a novel method and system for focusing a microscope. Though, at its broadest level of generality, it is applicable to all microscopes, it has particular advantage when associated in a system for automatic focusing, and it is presently considered most advantageous when the automatic focusing system is associated with a scanning system in which the object under inspection is translated under either a fixed or moving lens. The invention is especially applicable to instrument systems that operate under computer control such as optical scanners designed for reading biochips constructed on microscope slides or incorporated in a holder such as the Affymetrix "Gene Chip®". While having a special application in achieving low cost automated scanning, in which focus is established once per slide, the invention is also advantageous in performing dynamic focus.

The invention provides a simple and low cost technique to bring the relevant surface (typically the top surface) of a microscope slide or a biochip holder into the focal plane of a microscope by automatic motions of the instrument.

The invention also enables a plurality of objects to be viewed. According to a feature of the invention, each class of object with which the microscope is useful which may have e.g., different thickness or other dimensions, is provided a "special purpose location", the series of such locations being provided sequentially on the transport mechanism, so that the instrument is always ready to receive each type of object.

According to the invention, the focusing mechanism does not employ translation (Z motion) along the optical axis but rather simulates translation by tilting a plane, on which a flat side of the chip planar holder or the microscope slide is held, about a pre-established hinge axis, or preferably, by tilting about two pre-established, orthogonal axes. It is recognized that tilting a plane about a hinge located at "infinity" can always approximate translation of a small segment of a flat plane in the direction normal to that plane; it is now realized that, within the range of practical microscope instrument geometry and capability, rotating a plane coplanar with a flat object about a defined or pre-established hinge can effectively raise the level of a localized region or point on the plane in a direction essentially normal to its surface, to achieve the desired resolution for a microscope in a practical and low cost manner.

According to a preferred technique of the invention, a plane is fully determined by a line (the defined first hinge) and a point. With the first hinge defined to lie in a plane normal to the optical axis of the microscope, and the flat object being coplanar with it, focusing is achieved by moving "the point" along a line approximately parallel to the optical axis of the microscope.

In the preferred case, for instance, of scanning a micro lens objective relative to the object to trace a scan line, in which a series of single picture elements (pixels) are registered as the scan line is traced, in the event the top surface of the object inspected along that scan line does not lie in the plane so defined, provision is made according to the invention to rotate the "first hinge" along a pre-established hinge axis orthogonal to both the axis of that "first hinge" and the optical axis of the objective, in order to bring the top surface to be normal to the optical axis. This can be achieved by mounting the first hinge on a support which is coupled to the base of the microscope via a "second hinge" that permits a second motion, similar to the first.

Thus, motion for position along the optical axis and motion to maintain orthogonality are accomplished by actively tilting the plane of the object through an arc, or arcs, not by linear translation of the object.

Considerations of the depth of field and the field of view of the objective of a microscope (or the properties of a scanning microscope) guide the selection of the parameters that define such a plane and its two hinges and two movable points.

When a reference flat microscope slide of uniform thickness is located on such a plane, the first hinge and the point can be set such that a region of the top surface of the slide in registry with the optical axis of the microscope is in focus. The second hinge may be omitted especially when the spot size is large and offers sufficient depth of field to avoid frequent correction. If a flat microscope slide of different thickness is later used, adjusting only the movable point can bring the corresponding region of the top surface of that different slide into the focal plane of the objective within practical tolerances. The slide may then be advanced along the plane to bring different regions of the slide into registry with the optical axis.

Relative location of the pre-established hinge and point with respect to the optical axis of the objective is advantageously arranged to simulate the action of a lever, in which the movable point is made to move a relatively large amount compared to the resulting motion of the small segment of the plane that lies at the optical axis. As a result, a comparatively coarse, and therefore low cost, actuator, located at the long end of the lever, can be used to bring the surface of interest into focus by fine movements.

A signal from a sensor can be used to servo the actuator so that the desired region of the top surface of the slide will be in the focal plane of the objective, in line with the optical axis. A number of techniques, e.g. use of a strain gauge at the hinge, or use of optical, capacitive or inductive techniques, can be used to derive a signal to determine the tilted position of the top of the slide.

Also a number of conventional techniques can be used to decide that focus has been reached. The most common techniques analyze the image quality obtained though the microscope objective to drive the actuator until the tilting of the object achieves optimum position of "best focus".

In the various embodiments, when the microscope slide is mounted on a transport mechanism, the mounting surface of that mechanism is arranged to be parallel to the plane of lateral transport of the microscope slide.

In view of the above, according to one main aspect of the invention, a microscope having an objective with a restricted field of view about an axis for examination or treatment of an approximately flat object along the optical axis is provided, including a tiltable focusing member defining a support plane for the object, the member being mounted to rotate about a pre-established hinge axis to position the object on the member at the focal plane of the microscope, preferably about two hinge axes in the case of scanning in a line, each of which is substantially normal to the optical axis at a distance spaced therefrom, but at angles to each other, preferably orthogonal, and drive mechanisms for rotating the member about both hinge axes are effective to bring into focus the object supported by the member. It should be noted that no translation of the member is necessary for focusing purposes.

Preferred embodiments of this aspect of the invention have one or more of the following features.

The drive mechanism for the first hinge, e.g. the XX hinge, is a driver located outwardly along the tiltable member, more distant from the XX hinge than the position in which the optical axis of the microscope intersects the tiltable member, preferably the distance of the driver from the hinge axis being greater than about twice the distance of the optical axis from the hinge axis.

The drive mechanism for the second hinge, the YY hinge, is suitably located to permit the use of a coarse motion linear motor.

The positions of the drive mechanisms are controlled by an automated control system. In preferred embodiments of this aspect the control system includes a detector that senses the relationship of the object relative to the microscope. In certain preferred cases the detector is a strain gauge or an optical, capacitive or inductive position sensor that senses the height of the object. In a presently particularly preferred case, the detector comprises a light source and a sensor is arranged to determine the height of the object relative to the microscope on the basis of light reflected at an angle from the object. In other preferred cases a through-the-lens image analyzer is constructed and arranged to enable determination of best focus position.

In a preferred embodiment, the first hinge is defined by a reduced thickness of the mounting plate that supports the linear stage holding the object being inspected although in another case a pair of spaced apart flexures that support the tiltable member are employed, preferably the flexures being planar spring members.

The second hinge is similarly preferably defined by a reduced thickness of the mounting plate that supports the first hinge.

A laterally movable carrier is mounted on the tiltable member, the carrier arranged to advance the object, relative to the optical axis. Preferably the direction of advance includes motion in the direction of the radius of the tiltable member. Preferably, a linear guide rail is mounted on the tiltable member, the moveable carrier member movable along the guide, the carrier member having a planar surface for supporting a planar object, the planar surface of the carrier member being parallel to the linear guide. Also, preferably, a driver is arranged to position the carrier member under computer control.

In the form of a scanning microscope, the microscope is constructed and arranged such that the scan axis is normal to both hinge axes, preferably the scanning microscope comprising a moving objective microscope, presently preferred being a microscope in which the moving objective, preferably a micro lens weighing less than 2 grams, is supported upon an oscillating rotary arm that describes an arc generally centered on the axis of the second hinge and on a radial axis of the tiltable member. Preferably the objective has resolution of between about 0.5 and 10 micron and a depth of field of between about 2 and 200 micron.

In the form of a scanning microscope, a controller is provided, constructed to perform dynamic focus by varying the position of the drive mechanism during scanning, preferably the controller responding to through-the-objective image data, and most preferably including a system constructed to determine best focus data for an array of points during a prescan, to store this data, and to employ this data during microscopic examination of the object.

Another aspect of the invention is a microscope for examination of an object along an optical axis, which includes tiltable members defining a support plane for the object, the member being mounted to rotate about a pre-established first hinge axis to position the object on the member at the focal plane of the microscope, the hinge axis lying in a plane substantially normal to the optical axis at a distance spaced therefrom, and a drive mechanism for rotating the member about the hinge axis is effective to bring into focus the object supported by the member, the first hinge axis support being mounted onto a second member which itself is hinged along a second hinge axis substantially normal to both the optical axis and the first hinge axis, the microscope constructed and arranged to scan in a direction transverse to the radial direction of the tiltable member, and a laterally movable carrier is mounted on the tiltable member, the carrier arranged to advance the object, relative to the optical axis, in motion in the direction of the radius of the tiltable member.

In preferred embodiments of this aspect of the invention the scanning microscope comprises a moving objective microscope, preferably in which the microscope includes a flying micro-objective micro lens, and preferably in which the moving objective is supported upon an oscillating rotary arm that describes an arc generally centered on a radial axis of the tiltable member.

Another aspect of the invention is a support member for objects to be inspected by a microscope as described, having a lens member on an oscillating arm, oscillating about axis (Z—Z) in which the hinge axis X—X is located outwardly beyond the lens-carrying end of the arm, further from the axis ZZ than is the lens.

Preferred embodiments of all of the above aspects and features of the invention are microscopes in which the depth of field is between about 2 and 200 micron, and the drive mechanism is a driver located outwardly along the tiltable member, more distant from the hinge than the position in which the optical axis of the microscope intersects the tiltable member, preferably the distance of the driver from the hinge axis being greater than about twice the distance of the optical axis from the hinge axis.

According to another aspect of the invention a method of microscopic examination is provided comprising providing a microscope for examination of an object along an optical axis, the microscope including tiltable members defining a support plane for the object, the members being mounted to rotate about two defined hinge axes to position the object on the member at the focal plane of the microscope, both hinge axes lying in a plane substantially normal to the optical axis at a distance spaced therefrom, and a respective drive mechanism for rotating each member about its hinge axis, effective to bring into focus the object supported by the member, and under control of an automated control system, moving the movable member to bring the object into the plane of focus of the microscope.

Preferred embodiments of this aspect of the invention have one or more of the following features.

The object comprises biological material.

In certain cases, preferably the object fluoresces and the microscope is constructed to detect such fluorescence, and most preferably the object comprises an ordered array of nucleotides that may fluoresce, preferably the object comprises an ordered array of oligonucleotides or the object comprises an ordered array of deposits of nucleic acid fragments on a biochip or microchip slide.

According to another aspect of the invention, the method of performing quantified fluorescence microscopy comprising providing a microscope according to any of the above designs (such as that shown in FIG. 2A) calibrating the microscope with a calibrating tool having a surface layer of effective fluorophores (such as depicted in FIG. 7 using a calibrating tool such as the calibrating tool of FIG. 9, 10, 11 or 14), and subsequently scanning a slide or biochip having an array or micro array of specimens (as depicted for instance in FIG. 8).

According to another aspect of the invention, any of the microscopes as disclosed, are provided, in a novel way, with a series of dedicated positions, along the Y axis to receive different objects to be scanned, for instance, fluid-spotted microarrays of microscope slides, and biochip reaction modules such as the modules marketed by Affymetrix, Inc., under the brand "Gene Chip®".

BRIEF DESCRIPTION OF THE DRAWING

FIG. 1 is a diagrammatic, perspective view of a scanning microscope system incorporating a two axis tilt plane focusing mechanism, while FIG. 1B is a plan view.

FIG. 1D is a view similar to FIG. 1 having a modification, while

FIG. 1E is a magnified view of a detail showing the thinned section that acts as a hinge

FIG. 2A is a view similar to FIG. 2 of a fluorescence detecting microscope while

FIG. 4 illustrates optical height measuring techniques that act upon the top surface of a microscope slide for detecting its position, located as shown in FIGS. 1 and 1B, while

FIG. 6 is a diagrammatic illustration of a prescan for dynamic focus while

FIG. 11 illustrates a calibration slide being employed with a transparent support lying above the fluorescent layer.

FIGS. 12 and 13 illustrate biochips (Affymetrix Gene Chip®) for which the foregoing calibration slide is useful.

FIG. 16 illustrates a microscope slide carrying a membrane while

FIGS. 17 through 17C illustrate the formation of composite spots comprising multiple layers of biological material deposited upon for instance a microscope slide or membrane FIGS. 18 through 18C illustrate a similar procedure in which the second layers are comprised of smaller spots than the first spots deposited, with a number of such smaller spots being applied to one given large area spot.

FIGS. 19 through 19C illustrate forming a product similar to that of FIGS. 17 through 17C but by "upside-down" action.

DESCRIPTION OF THE PREFERRED EMBODIMENTS

Figure 2:
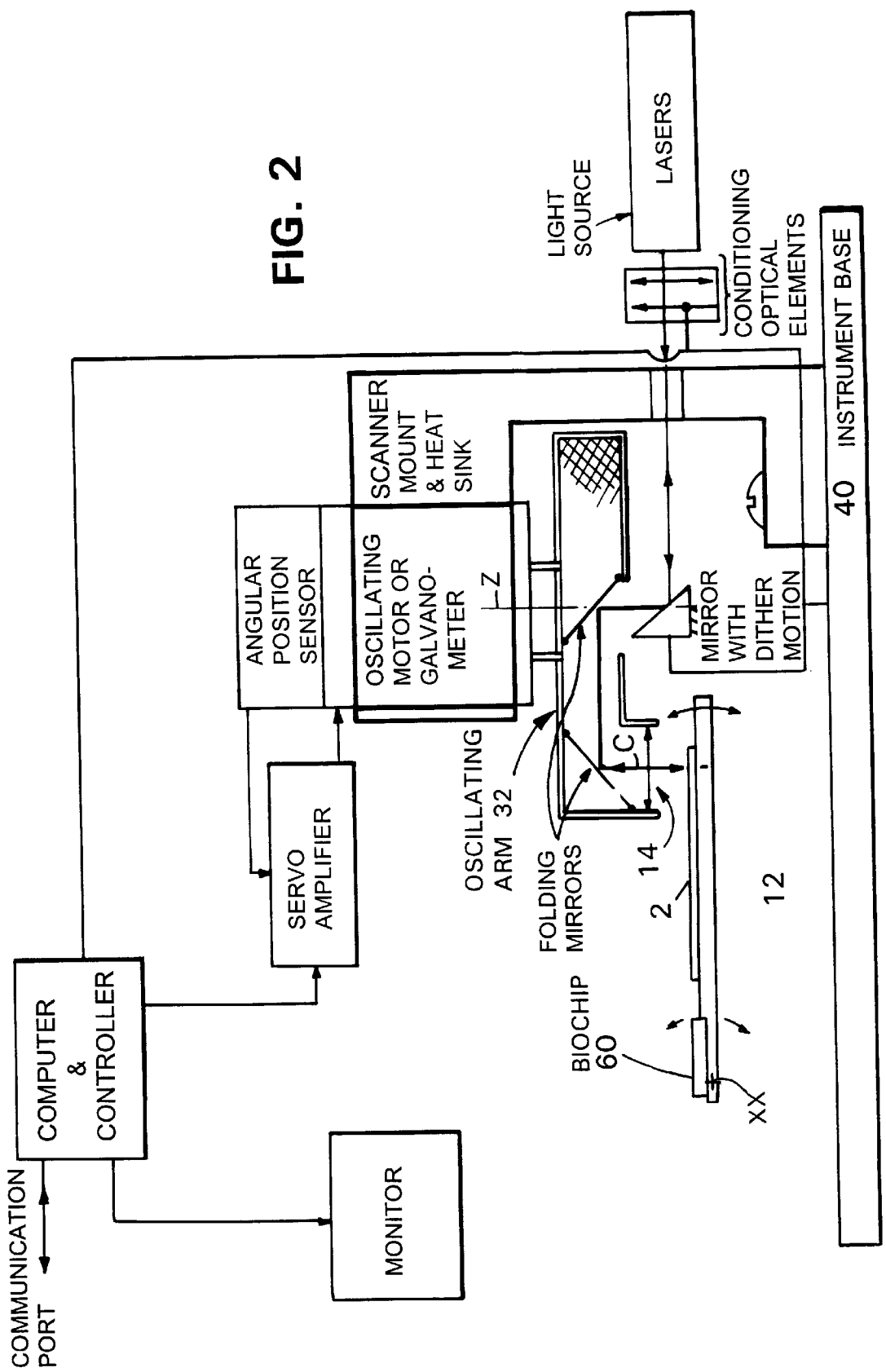
FIG. 2 is a diagrammatic side view of a scanning microscope system with which the focusing system of FIGS. 1–1C or 1D is combined.

The invention will be described as it applies to the presently preferred embodiment, which includes, in combination, a rotary oscillating flying micro-objective scanning microscope such as shown in FIG. 2 and described in more detail in the patent applications related to scanning cited above, which are hereby incorporated by reference.

Figure 2A:
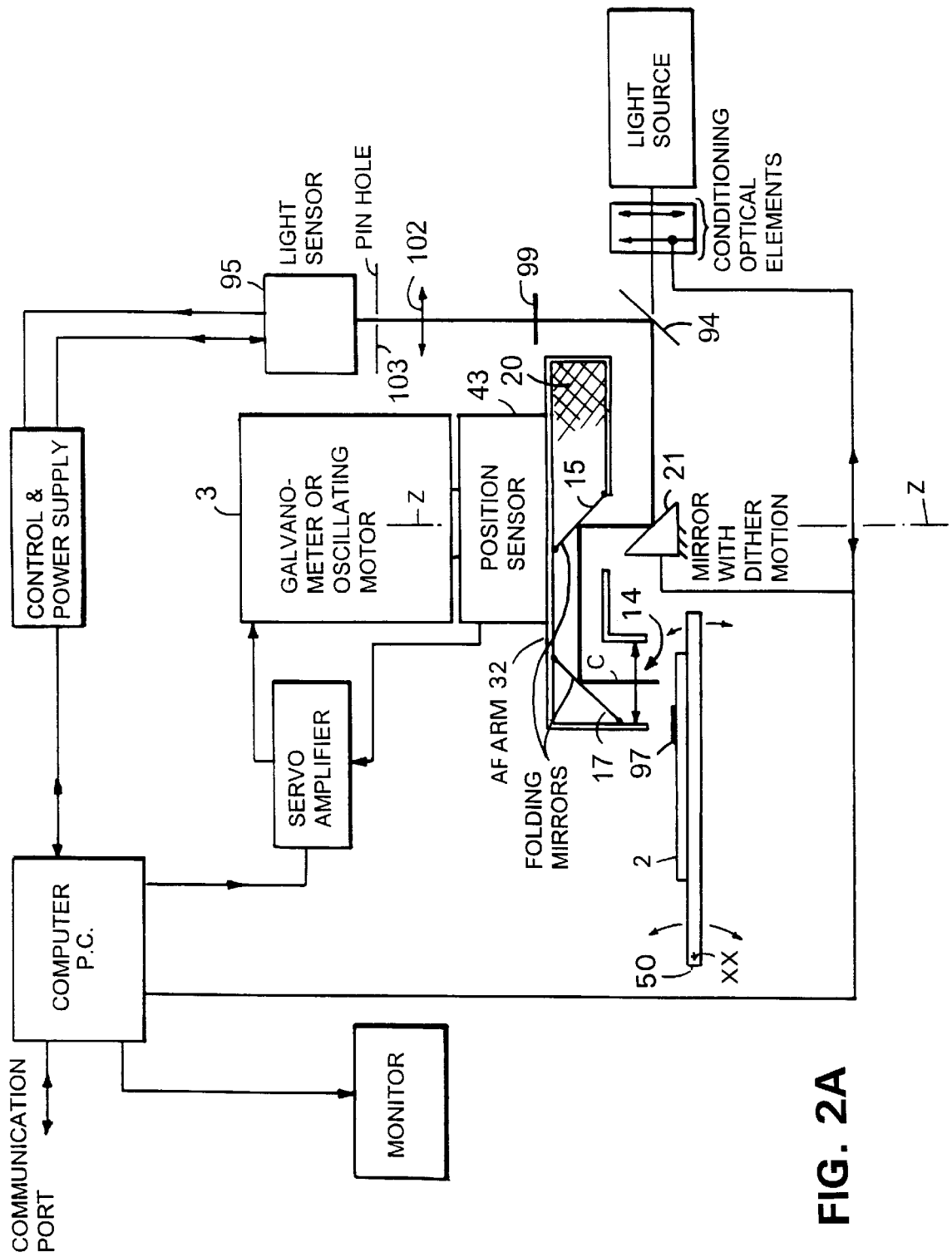

Referring to FIGS. 2 and 2A, it is sufficient to note that objective-carrying arm 32 rotates in rotary oscillating fashion through an arc of e.g. 60 degrees about rotational axis ZZ that is normal to the nominal plane of the microscope slide 2 or biochip 60. The arm carries a low mass micro-objective lens 14, e.g. a micro lens of weight less than about 2 grams, sized to detect a single picture element at any data collection point. The optical axis C at a radial distance from the axis of rotation ZZ, produces a range of excursion E sufficient to scan the width of the microscope slide 2 or biochip 60, provision for both of which are provided on the microscope. The lens typically has a large numerical aperture. An appropriate fixed laser light source and detector are arranged to communicate with the objective lens 14 along an optical path along the axis of rotation ZZ of the arm, via folding mirrors carried on the arm. In this manner the optical axis C of the lens is maintained normal to the nominal surface of the object throughout its scanning motion, to perform so-called "on-axis" scanning. While the lens is carried back and forth in its arc, the microscope slide or biochip is gradually advanced under the arc of the lens in the direction of axis Y, so that the entire slide is examined in a short time. Dither motion (FIG. 2) of a mirror in the optical path can be used to broaden the curve of the effective arc path of the lens to reduce overlap in successive scans, and for high speed scanning, the object may be read in both forward and backward excursions. By suitable computer techniques, the data for the points of resolution are recorded throughout the scan of the slide 2 or biochip 60 and are employed to form an image by conventional computer techniques.

Figure 1:
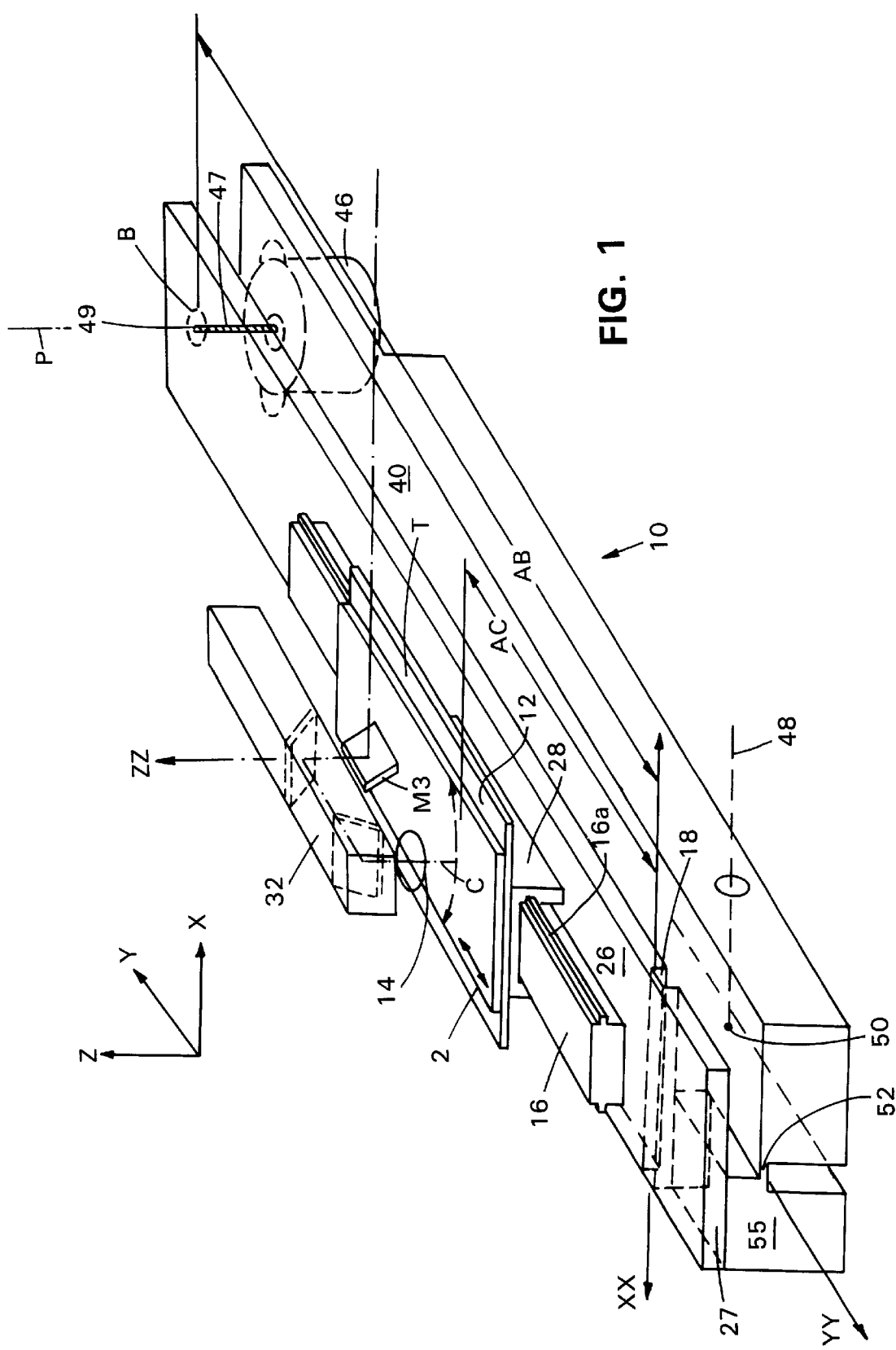
Figure 1A:
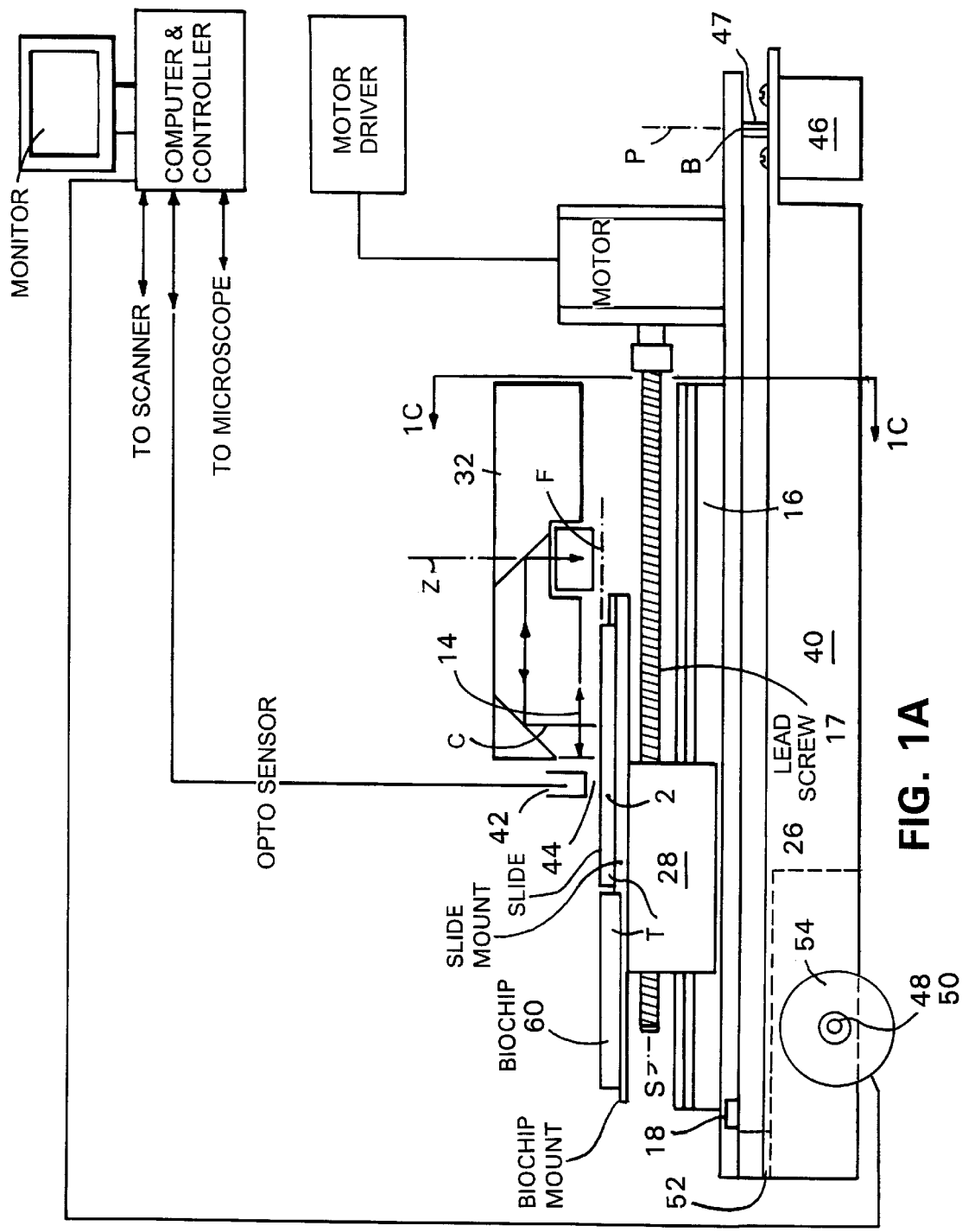
FIG. 1A is a side view.
Figure 1C:
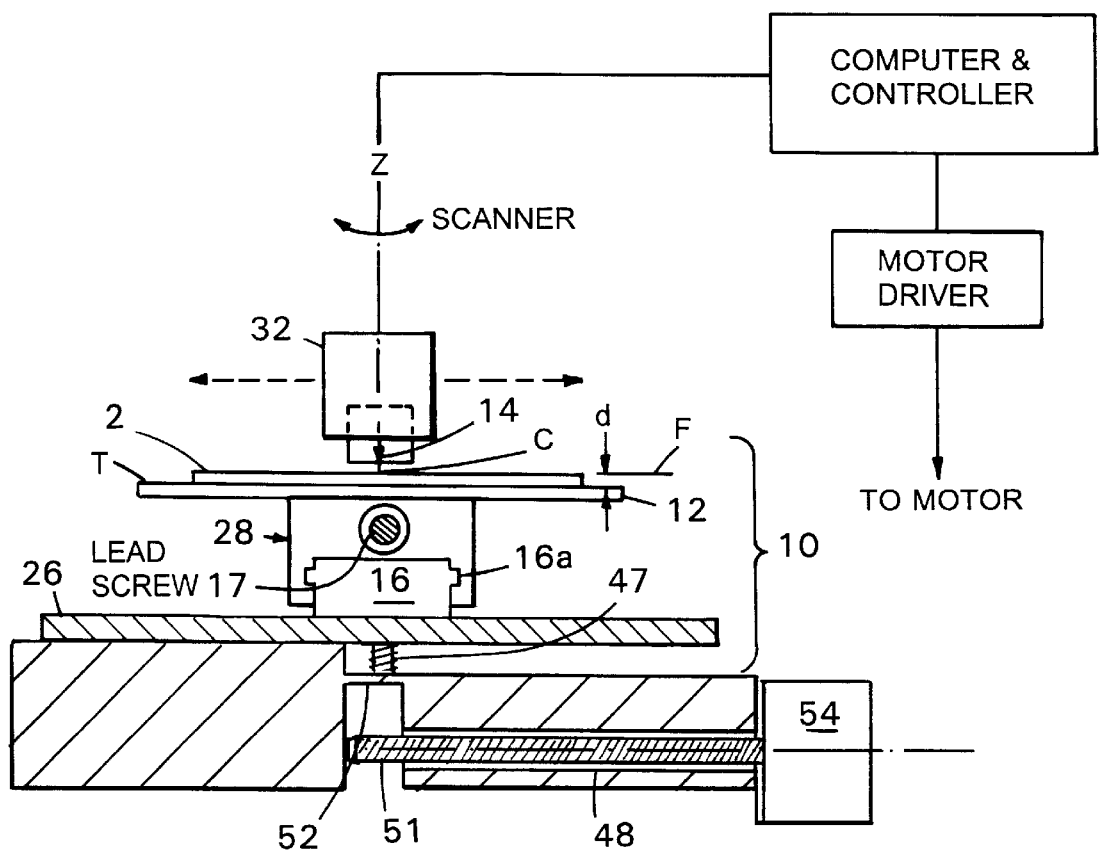
FIG. 1C is a cross sectional view of the mechanism of FIG. 1.

In the preferred embodiment of the tilt focusing mechanism 10 of FIGS. 1–1C, the microscope slide 2 or biochip 60 are held in respective provided positions. As shown in FIG. 1 A, the biochip mounting surface is lower than that of mounting surface for the slide to accommodate greater thickness while locating its top surface to be scanned approximately at the same plane as the microscope slide.

Platform 12 is itself part of moveable carriage 28, which is mounted to move axially on guide rail 16, as positioned by motor-driven lead screw 17.

Slide mount platform 12 is typically an anodized aluminum plate, which is installed under the objective 14 of the oscillating flying objective microscope arm 32, at a distance d (FIG. 1C) greater than 1 mm (the nominal thickness of a microscopic slide) away from the focal plane F of the objective.

As shown in FIGS. 1 to 1C, rail 16 is mounted on first hinged carrier plate 26 which is positioned on second hinged carrier 55. Reduced thickness of plate 26 at slotted region 18 provides an integral flexible joint that defines hinge axis XX. The optical axis C of the microscope is closer to axis XX (distance AC), than is the third point B, which lies at distance AB from hinge axis XX. The three points are located in a bi-symmetric fashion with respect to the axis of rotation C of the flying objective arm 32 as shown in the plan view, FIG. 1B.

The configuration shown locating the hinge axis outwardly of the end of arm 32 carrying the lens locates the fixed part of the structure, (27, FIG. 1) as a suitable apron that can facilitate automated loading and unloading of microscope slides and bio chip reaction modules.

Carriage 28, carrying the microscope slide, is motor driven, the motor and lead screw being shown in FIGS. 1A and 1B. The top surface T of the microscope slide 2 or biochip 60 is precisely parallel to axis S, the axis of lateral motion of the slide as defined by guide surfaces 16a of rail 16. Any deviation is equivalent to defocusing in this embodiment.

Along axis XX, plate 26 is flexurally connected to movable region 55 of base 40 of the instrument via a linear flexible joint, here in the form of a long flexure formed by an integral reduced thickness region of metal plate 26, formed by a transverse slot as shown, the proximal portion of the plate 2 serving as the ground, which is rigidly connected to proximal region 55 of base 10. The more remote third mount, B, is raised or lowered by push rod 47 for producing focus as will be described below.

Referring to the embodiment of FIG. 1D, which is otherwise substantially similar to FIG. 1, the elongated flexure establishes the hinge axis XX in substantial alignment with the plane of the top surface of the microscope slide 2. Point B is acted upon by pusher stepper motor 46 acting through push rod 47. Preferably an outboard compression spring, not shown, ensures secure contact between push rod 47 and point B of plate 26.

In many cases it is advantageous that arc E (see FIG. 3B) delineated on slide 2 or biochip 60 be in a plane normal to the optical axis C (and axis of rotation ZZ of the scanner arm 32). Particularly in the case of wide excursions, if the reference plane of the slide or biochip is not parallel to the top surface, provision is made to incline the first hinge axis XX to correct this discrepancy, while hinge 18 is mounted via region 27 onto region 55 of base 10, region 55 is itself flexurably connected to base 10 via an integral, reduced section 52 slot creating a second elongated flexure 52, which is preferably located symmetrically with respect to the slide or biochip and normal to both the ZZ and XX axes.

Linear motor 54 (see FIG. 1A, similar to motor 46) drives pusher 50 through hole 48 to provide controlled motion of region 55 of base 10. Consequently axis XX can be slightly rotated to cause the target mounting surface 12 to be normal to optical axis C of the objective as it oscillates in its rotary arc along path E (FIG. 12), about axis ZZ.

The motion of point B along axis P, to achieve a given focus correction, is defined by its distance from the optical axis C of the objective as well as the location of hinge axis XX with respect to the objective axis.

Figure 3A:
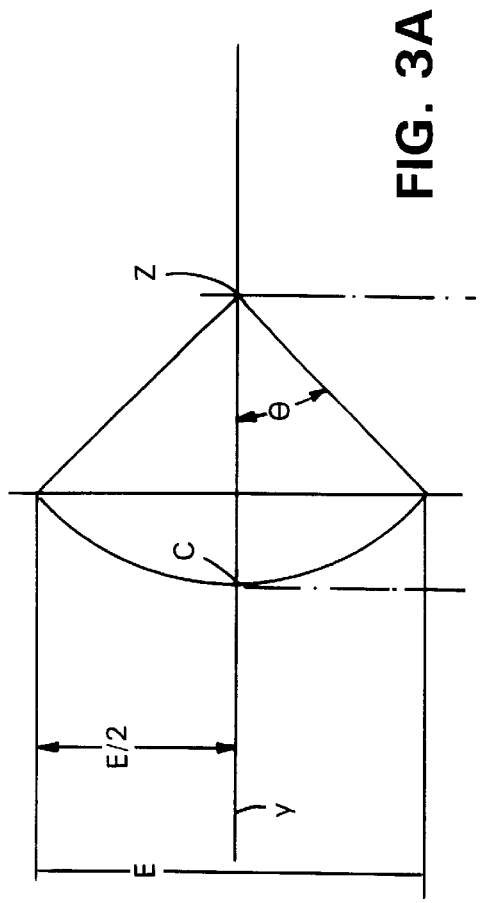
FIGS. 3A and 3B are diagrams that help define the focus variation caused by the angular oscillating motion of the scanning objective microscope of FIG. 2 or 2A associated with the XX tilt plane focusing mechanism of FIGS. 1–1C.
Figure 3B:
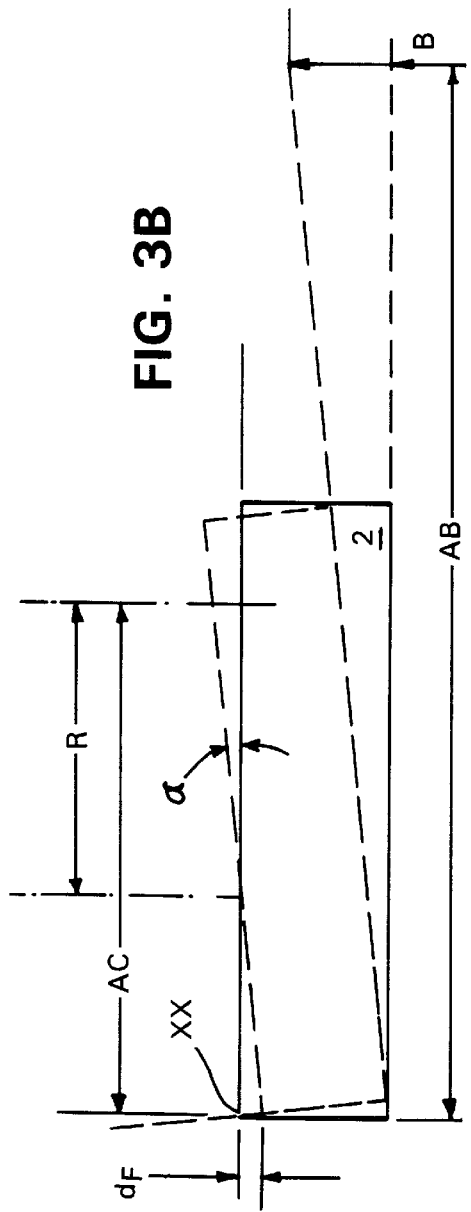

FIGS. 3A and 3B illustrate the focus variation dF as a function of angular position of arm 32 over a slide 2 tilted about axis XX, in consideration of the variation in thickness permitted for standard microscope slides. It can be seen that:

$dF = R * \tan \alpha * (1 - \cos \theta)$ where $\alpha$ and $\theta$ are identified on FIGS. 3A and 3B. In a specific implementation of the preferred embodiment, the following values are employed:

R=25 mm, the radial distance of objective 14 from the axis of rotation ZZ of the swing arm 32.

$\theta$=+/−26 degrees, the angular excursion of arm 32 from its center position on axis YY.

AC=60 mm, the distance of the extreme position from hinge axis XX of the optical axis C of the lens 14 carried on arm 32.

$\alpha$=Slide thickness variation $\Delta_t \div AC$=+/−0.150/60=+/−0.0025 radian.

This produces focus variation dF=+/−6.32 micron or a total of approximately 20% of the depth of field of the objective 14 in the case at hand. (The miniature flying objective lens 14 in the case at hand has a depth of field of about 50 microns).

Figure 5A:
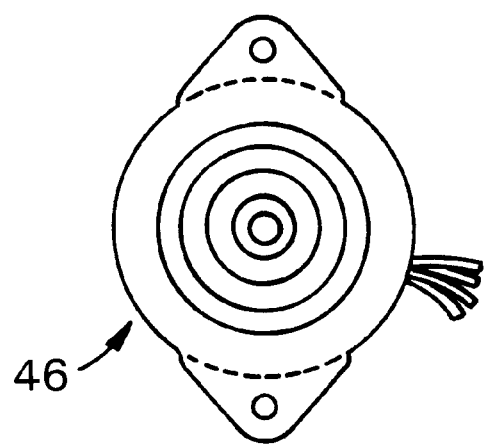
FIGS. 5A and 5B are end and side views of a linear stepper motor employed as a pusher mechanism in the system of FIGS. 1–1D and FIGS. 2 and 2A.
Figure 5B:
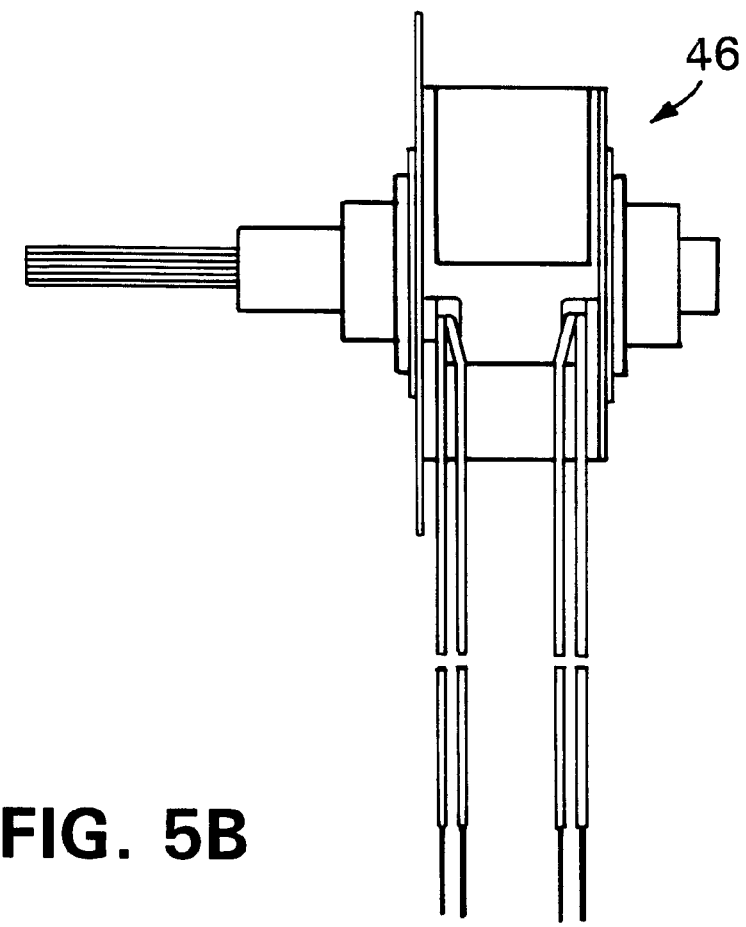

In the preferred embodiment where the optical resolution is approximately 10 micron and the depth of field 30u, pusher 46 (See FIGS. 5A, 5B) is a linear stepper motor, e.g., a Haydon 46647-05 stepper motor available from Haydon Switch and Instrument, Inc. of Waterbury, Conn., having 0.0005 inch (3.175 micron) motion per step.

With the distance AB from the pusher 46 to hinge axis XX of 265 mm, a 4.4 to 1 motion reduction is obtained, which yields a resolution at the objective of approximately 0.75 micron introduced by the pusher. The uncertainties of the digital system then cause a possible error of 1.5 micron of the slide position under the objective. This is approximately 5% of the budgeted focal range of the preferred embodiment. The simple and inexpensive system shown is thus capable of automatically focusing a new biochip or slide when it is introduced to the system.

Figure 2B:
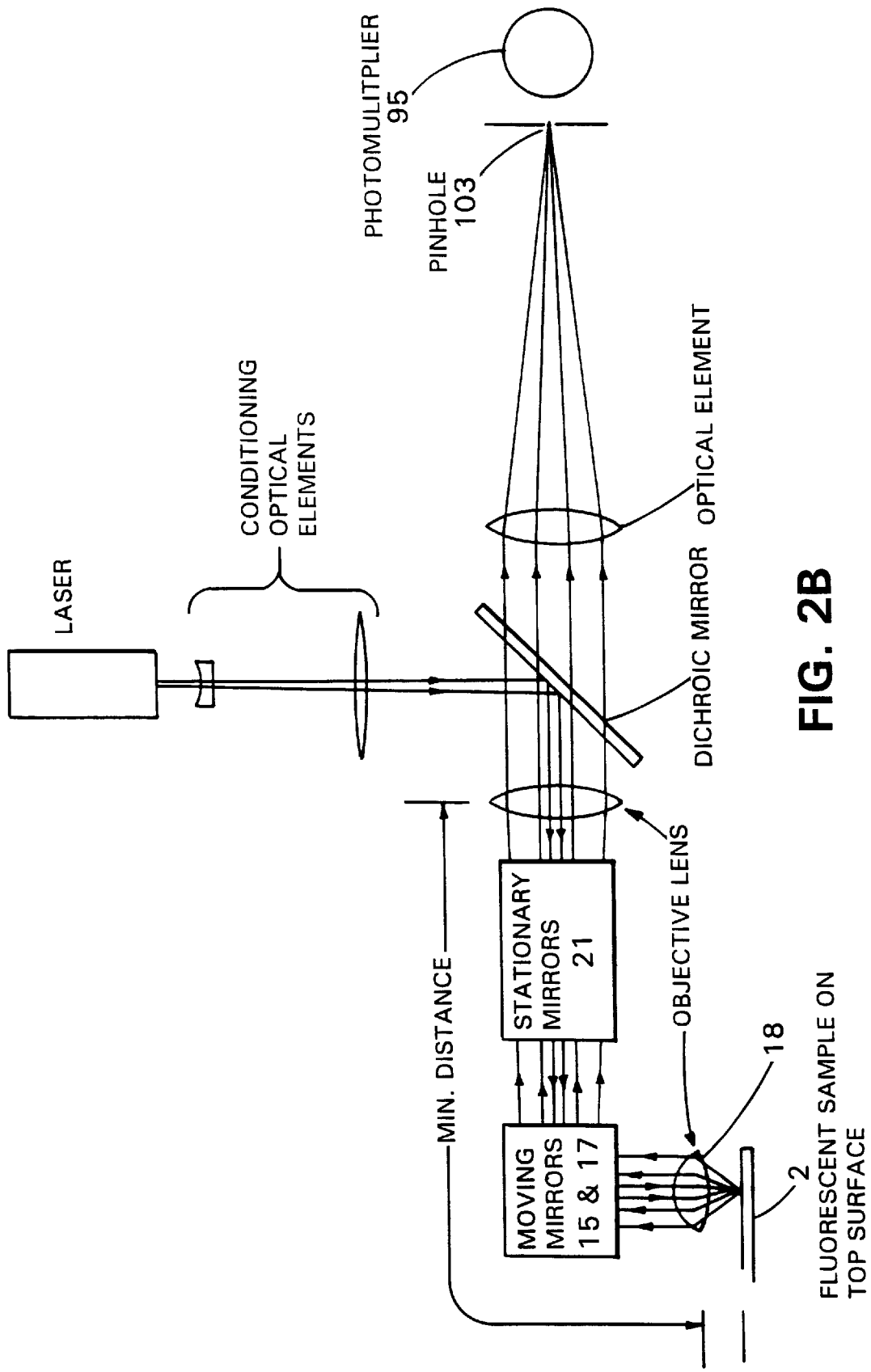
FIG. 2B is a diagram of its optical path.

The system is particularly effective for examination of ordered arrays of biological material such as biochips. In one case an ordered array of oligonucleotides that may be hybridized with fluorescently labeled material is inspected, using the microscope of FIGS. 2A and 2B. The individual specimens may be present in array densities for instance of 100 to 2000 or more specimens per square centimeter. An example would be biochips sold by Affymetrix, Inc., under the brand GeneChip®, as shown in FIGS. 12 and 13. Such biochips may be pieces of borofloat glass fixed on black plastic cartridges permitting hybridization steps when connected to a fluidic station. Typical dimensions may be 1.5 inch×2.75 inch×0.290 inch.

On the surface of the glass (inside) are attached oligonucleotides as a matrix of features in the active area and a deposited chrome border is used as a position control.

The active area may for instance have maximal size of 12.8×12.8 mm$^2$ or a maximal size of 5.5×5.5 mm$^2$. The feature may have a minimal size of 20 $\mu$m×20 $\mu$m. FIG. 12 pictures a biochip "49" while FIG. 13 pictures a biochip "169".

Figure 15:
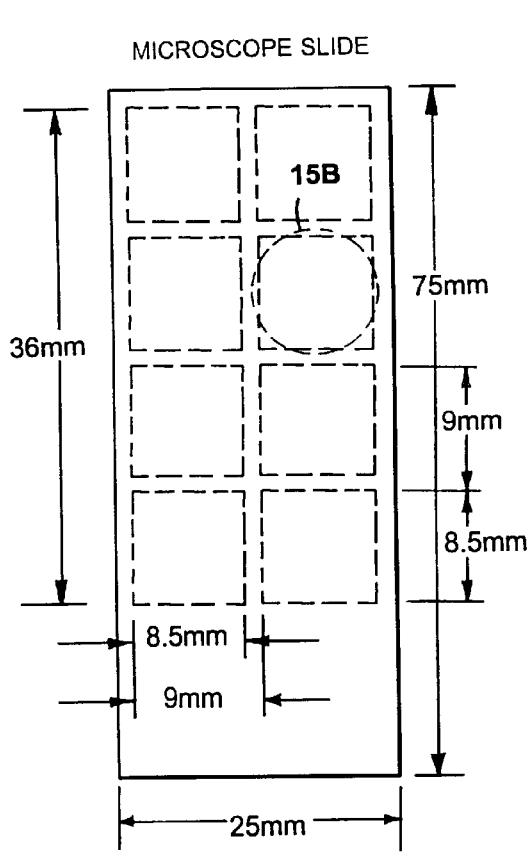
FIGS. 15, 15A and 15B illustrate a microscope slide with which the calibration tool of FIG. 14 is useful.
Figure 15A:
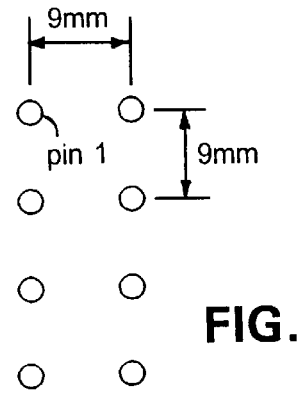
Figure 15B:
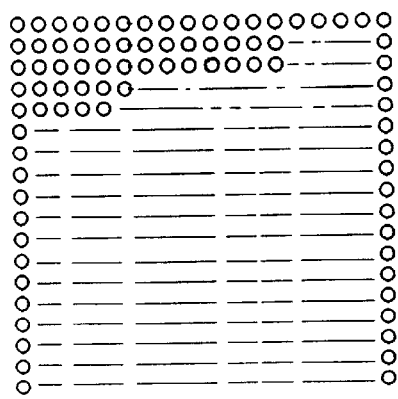
Figure 16A:
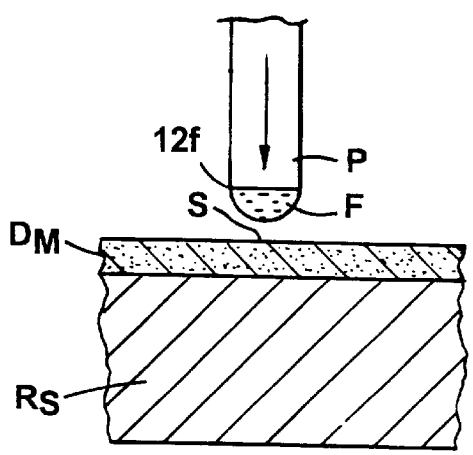
FIGS. 16A through 16D illustrates steps of forming one of a multitude of spots of biological material, for instance, upon the membrane for later inspection by the scanning microscopes according to the invention.
Figure 16B:
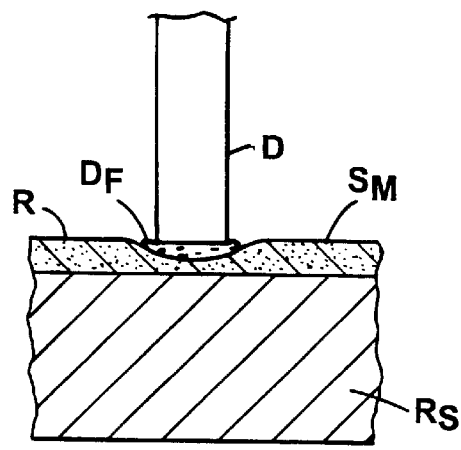
Figure 16C:
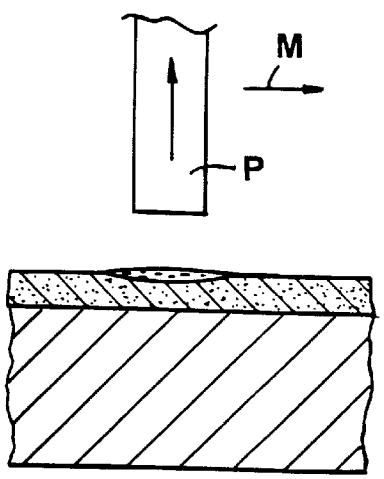
Figure 16D:
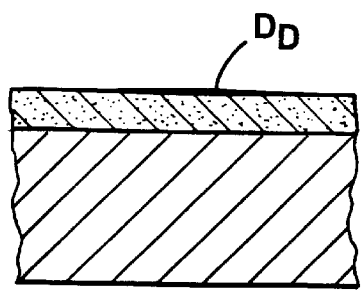
Figure 16:
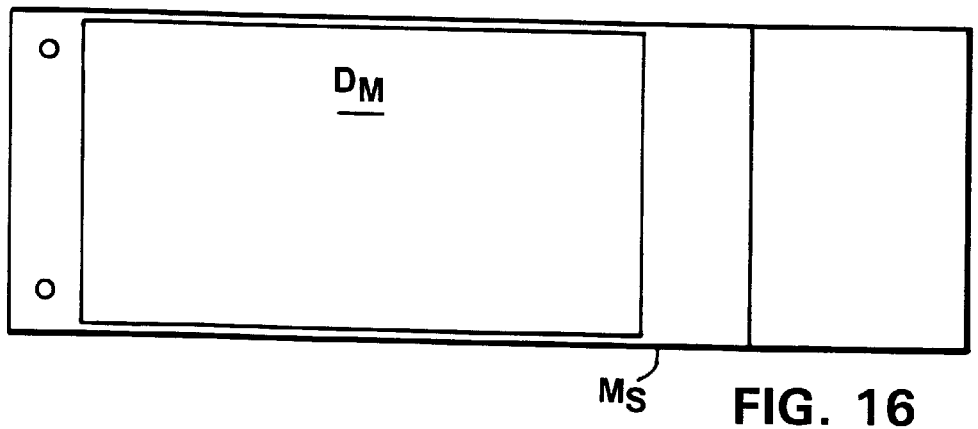
Figure 20:
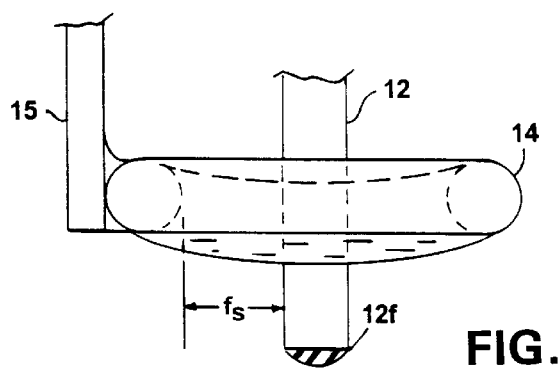
FIG. 20 illustrates a deposit assembly, specifically the Genetic Microsystems "Pin and Ring™" 20' assembly while FIGS. 20A through 20D illustrating the operation of the deposit device
Figure 21:
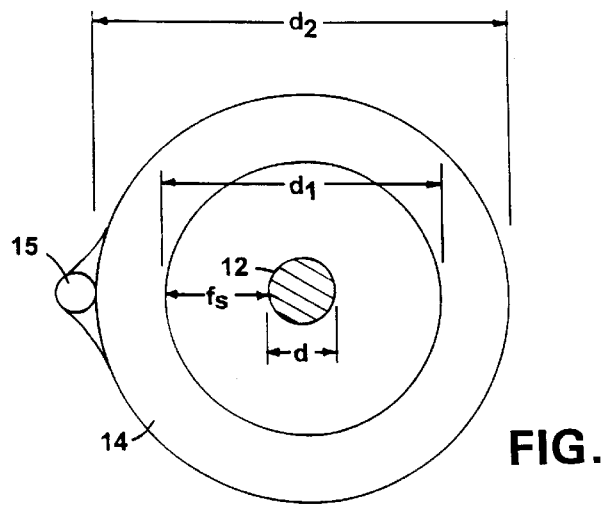
FIG. 21 is a plan view of the device.
Figure 20A:
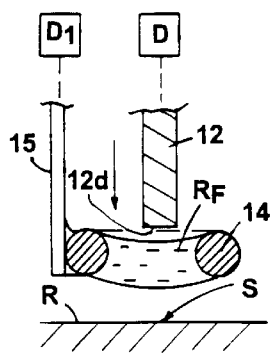
Figure 20B:
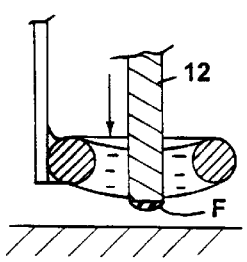
Figure 20C:
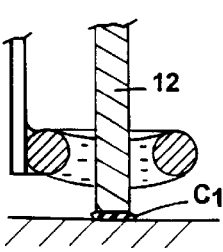
Figure 20D:
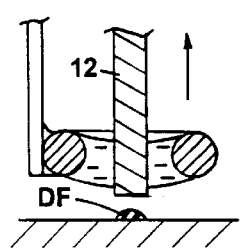

In another case an ordered array of nucleic acid fragments is examined, for instance as deposited by the arrayer described in co-pending U.S. Patent Application, U.S. Ser. No. 09/006,344, filed Jan. 13, 1998, which, among others of similar title, cited above are hereby incorporated by reference. Referring to FIGS. 15, 15A and 15B, spots of liquid containing the bio material are deposited by suitable pins. FIGS. 16–16D picture a pin depositing on a membrane $D_m$ carried on a slide-form carrier. FIGS. 17–19 show various deposit techniques for superposed layers, spots on spots. FIGS. 20–20D depict a deposit mechanism comprising a mobile sub-reservoir associated with a deposit pin sold under the mark "Pin and Ring Technology"™ by Genetic MicroSystems, Inc.

For dealing with such microarrays, a number of modalities can be employed to detect the position of the top surface T of the slide or biochip or other portion of the moving mechanism. Also, the position detector and the pusher actuator may be linked as a position servomechanism.

Figure 4:
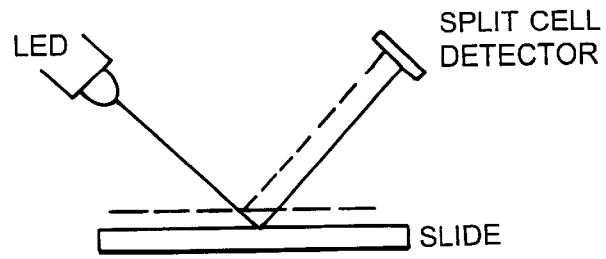

FIG. 4 exemplifies a means for detecting the height of the top surface of a slide. The system of FIG. 4 employs a light emitting diode (LED) and a split photocell detector, according to well known techniques in which light from the LED strikes the surface at an angle and is reflected to the detector, the size of the angle depending upon the proximity of the slide of the LED. The detector detects the position of the top surface essentially along the Z axis (parallel to axes ZZ and C of the prior figures), based upon trigonometric considerations. After positioning of the slide or biochip, the control system extinguishes the LED during operation of the instrument, to avoid stray light interference. Similar embodiments employing capacitive and inductive position sensors, associated with a capacitive or inductive reference device associated with the slide, can be employed.

Figure 4A:
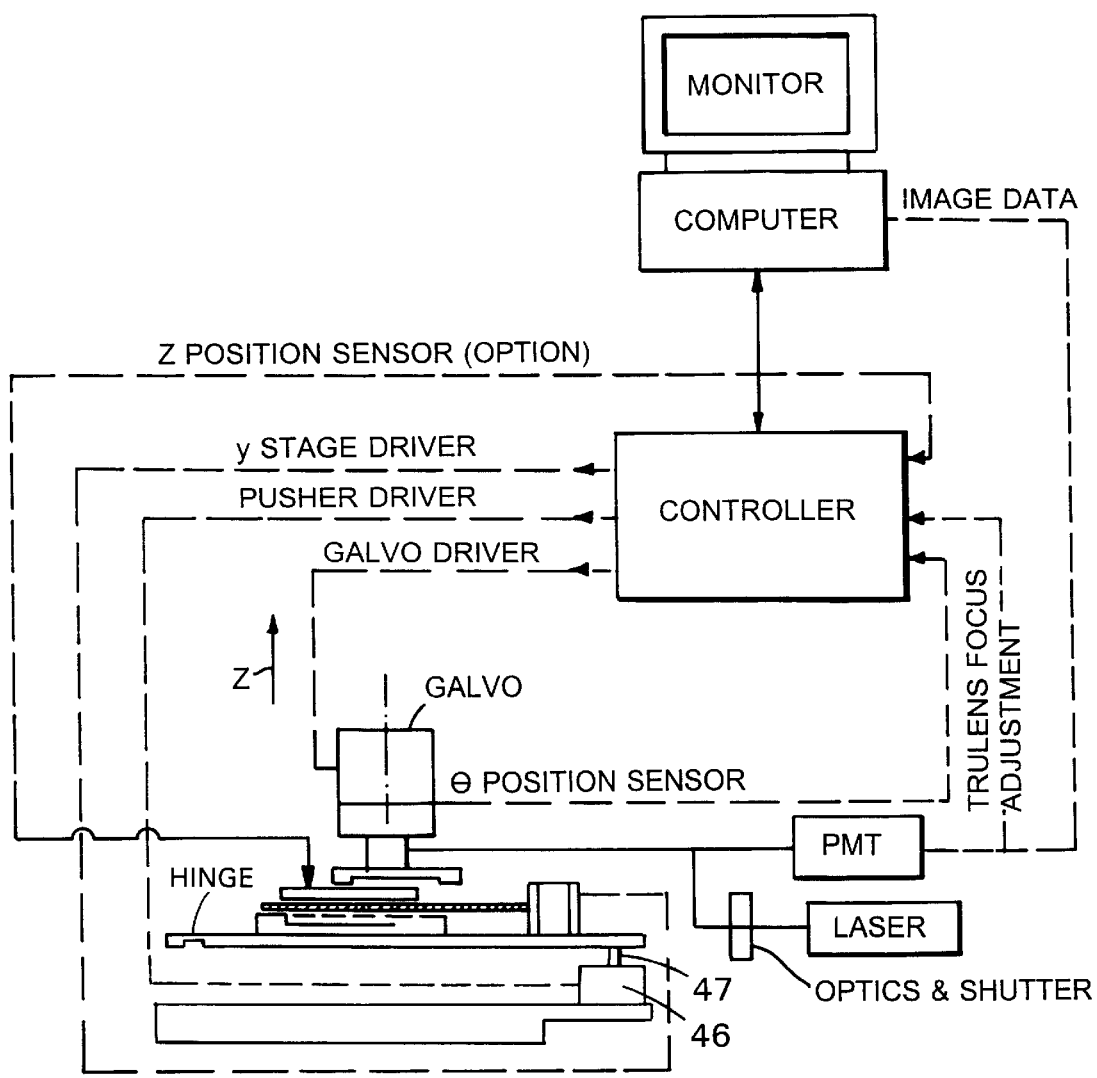
FIG. 4A is a diagram of a control system that employs the system of FIG. 4.

Referring to FIG. 4A, a detector for the height of the top surface of the slide 2, e.g. the detector of FIG. 4, feeds the Z position information, i.e. the distance of top surface of the slide or biochip from the objective, to a controller which, by servo techniques, drives the pusher 46 to bring the slide or chip into the proper position for focus. The controller also controls pusher 54 to ensure focus at all position of arc E as well as the Y stage driver and the galvanometer that drives the oscillating arm 32. The controller also manages the collection of data from the objective lens which is input to a computer which receives the detected data and produces the desired image on a monitor.

The focusing technique described can advantageously be used with conventional microscopes and other types of scanning microscopes, pre-objective or post objective or translation objective microscopes, etc. It also has application to other microscopic systems, such as laser illumination and laser systems for treating objects of varying dimension.

Figure 6:
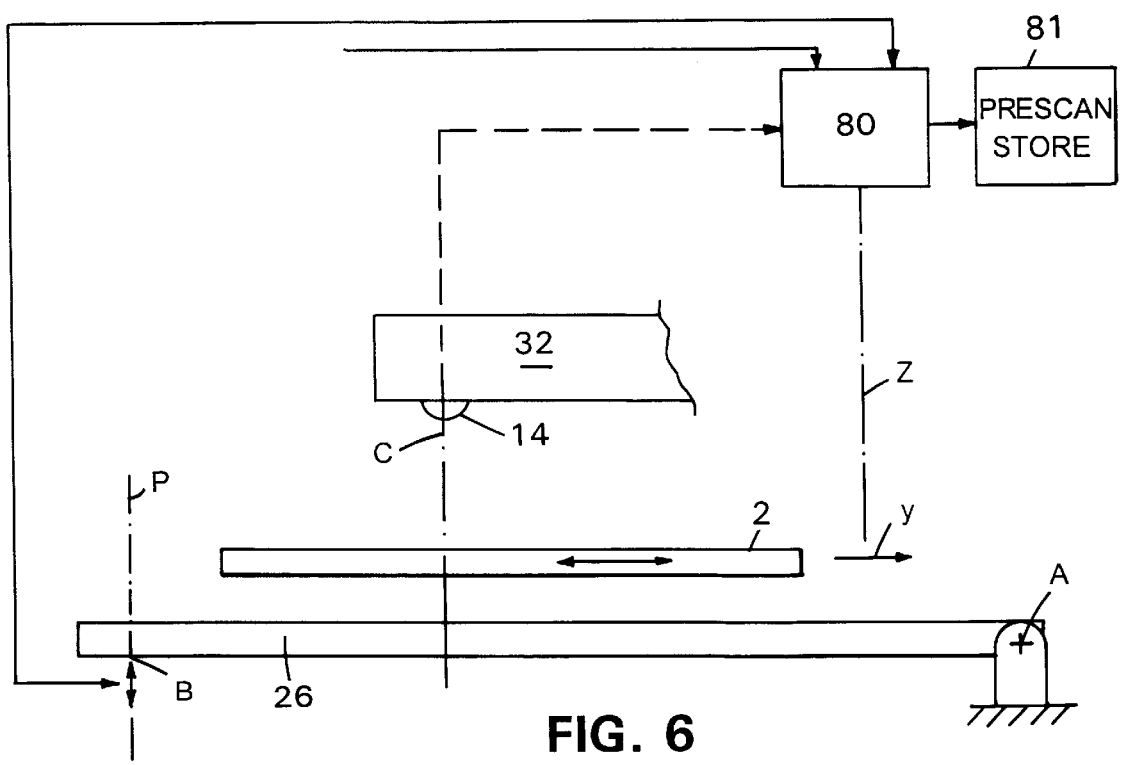

In cases where higher resolution is desired, thus limiting the depth of field of the microscope, a system similar to that of FIGS. 1, 2 and 2A is provided that implements a dynamic focusing techniques. For example, as depicted in FIG. 6, prescan analysis of the topology of the surface of the microscope slide or biochip is performed.

The slide 2 or biochip is gradually advanced in direction Y while the flying objective lens 14 is scanned in arcs over the slide or chip by oscillation of arm 32 about axis ZZ. During the prescan, the pusher 46 is exercised to dither the height of point B up and down under control of prescan analyzer 80, thus raising and lowering the object to vary focus.

By analysis of image data collected through the lens for an array of locations over the slide, the prescan analyzer determines the height of best focus for each location. This data is stored, for access during the examination scan.

Figure 6A:
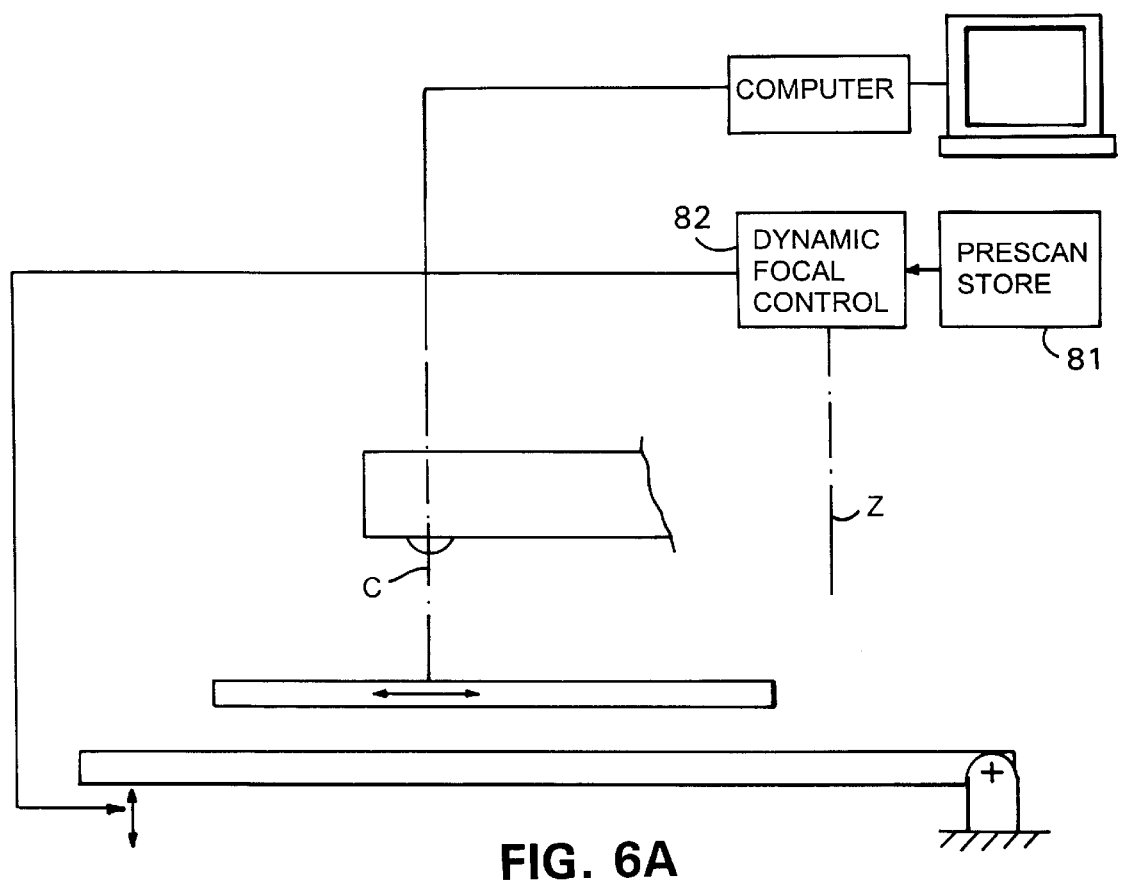
FIG. 6A is a similar diagram of the system performing dynamic focus employing stored prescan data.
Figure 7:
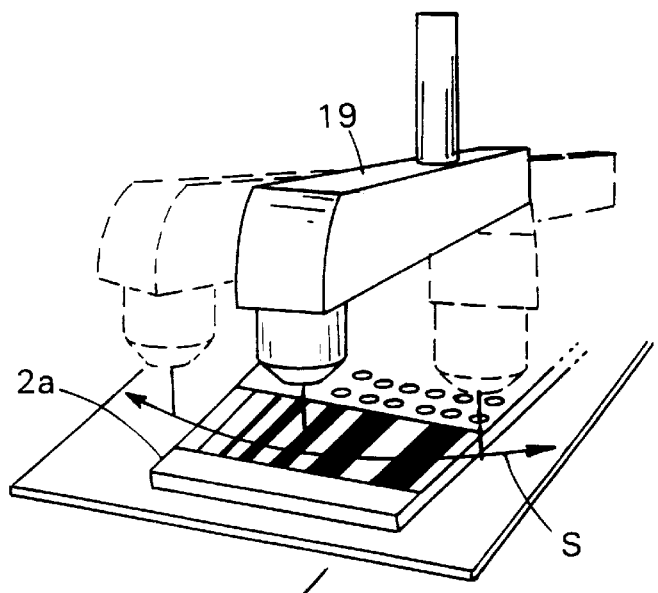
FIG. 7 depicts the microscope of FIG. 1, 1D, 2 or 2A used with a calibration slide for calibrating the instrument.
Figure 8:
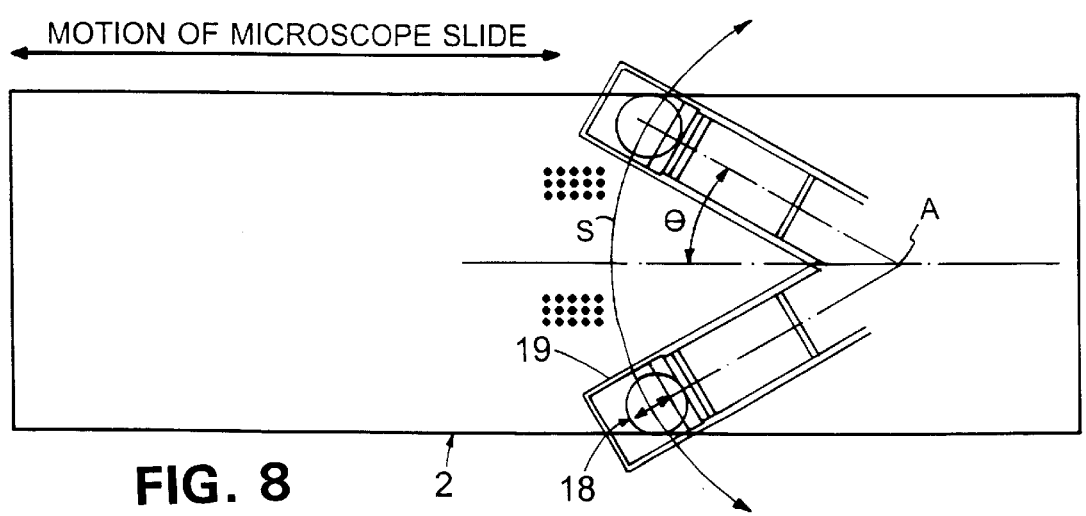
FIG. 8 is a plan view illustrating scanning of a microscope slide following calibration.
Figure 10:
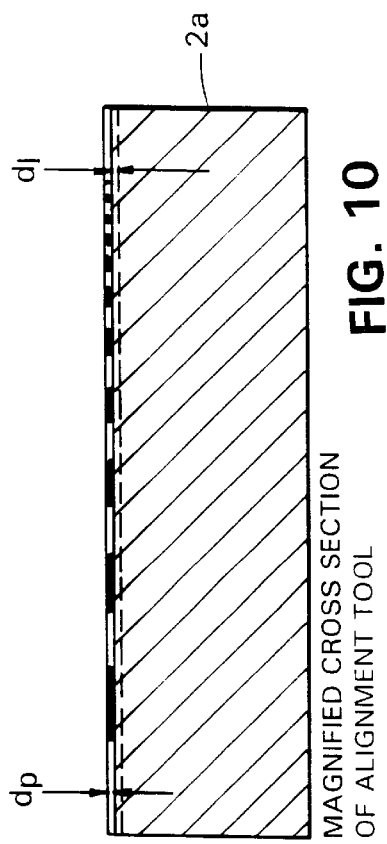
FIG. 10 is a cross section taken on line 10—10 of FIG. 9.
Figure 9:
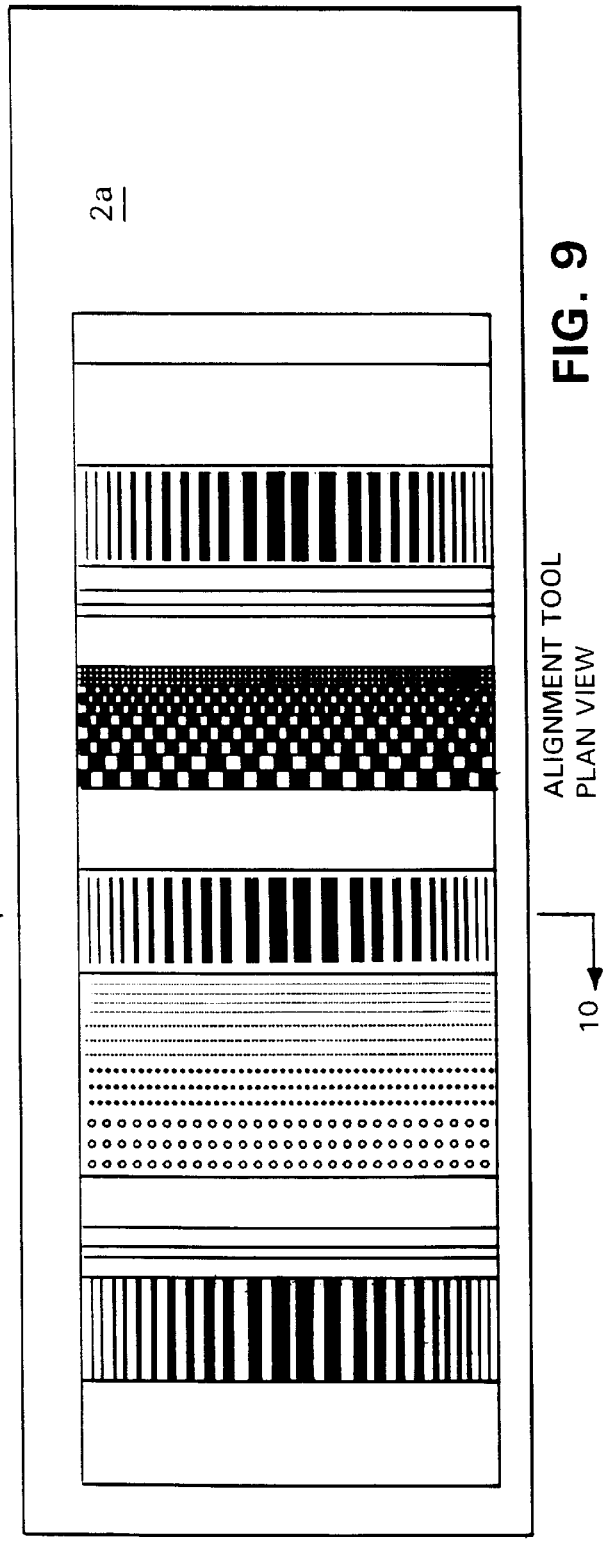
FIG. 9 is a plan view of a calibration slide useful for fluorescence detection microscopes.
Figure 14:
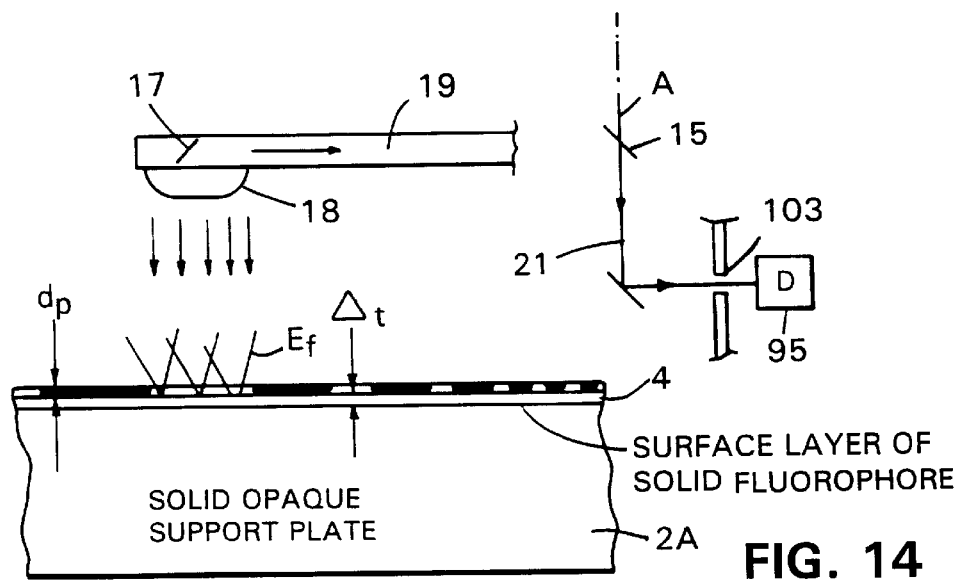
FIG. 14 illustrates another calibration slide in which the fluorescing material is at the exposed surface of the reference tool.

Likewise, pusher 54 can dither the orientation of the slide or chip support about the YY axis. Thus a similar process is implemented at extreme positions of arc E and pusher 54 aligns axis XX to have surface T normal to optical axis C. One technique for doing this is by analyzing the frequency content of detected signals for features of the object imaged during the prescanning, in relationship to the position of the point B that is undergoing dithering. Such techniques are known, see for instance the discussion in U.S. Pat. No. 6,201,639, which has been incorporated by reference. Thus the position of point B for best focus for a given location on the slide may be selected as that position in which high frequency content of the signal is maximized. Thus, during the prescan, a set of data is stored representing the topology of "Best Focus" over the area of the microscope slide. Referring to FIG. 6A, during the subsequent examination scan, the stored prescan data is employed by a dynamic focus controller to elevate and lower point B as the scanning proceeds to bring the respective locations on the slide into best focus. While a fixed tilted position about axis YY will normally Ice, it is also possible to control that orientation dynamically based on present data, e.g. in the case that warpage of the surface out of planarty has been detected, It is important to realize that the tilt focus technique described can be an important part of a practical and relatively inexpensive system capable of producing quantified fluorescence microscopy. For this purpose a critical feature is the use of a calibration tool as shown in FIGS. 9, 10 and 14 suitable for e.g. the Affymetrix biochip module and in FIGS. 9, 10 and 14 for fluid deposited arrays. Such calibration tools are described in U.S. application Ser. No. 09/500,548 entitled "Quantified Fluorescence Microscopy", filed on Feb. 6, 2000, the full disclosure of which has been incorporated by reference.

It will also be understood that provision can be made for heating, cooling or maintaining a precise temperature of the slide or biochip during examination. For that purpose the standard mounting plate for the slide or biochip is defined by a filler plate which can be replaced by a thermoelectric cooler or heater plate of identical dimensions.

Numerous other embodiments are of course possible and are within the scope and spirit of the claims.

What is claimed is:

1. A microscope having an objective lens with a restricted field of view about an optical axis for examination or treatment of a portion of an object lying at the optical axis, including a tiltable focusing member defining a support plane for the object, the focusing member being mounted to rotate about a pre-established hinge axis to position said portion of the object at the focal plane of the microscope, the hinge axis lying in a plane substantially normal to the optical axis at a distance spaced therefrom sufficient that rotation of the portion of the object at the optical axis sufficiently approximates translation along the optical axis to enable focusing, a drive mechanism for rotating the focusing member about the hinge axis effective to bring into focus said portion of the object, a mechanism for rotating the plane about an axis orthogonal to the optical axis and the hinge axis so that the object can be scanned on a line substantially in a direction parallel to the hinge axis, and a laterally movable carrier mounted on the tiltable focusing member, the carrier being arranged to advance the object relative to the optical axis.

2. The microscope of claim 1 in which the direction of advance includes motion in the direction of the radius of the tiltable focusing member.

3. The microscope of claim 1 in which a linear guide rail is mounted on the tiltable focusing member, the moveable carrier member movable along the guide rail, the carrier member having a planar surface for supporting a planar object, the planar surface of the carrier member being parallel to the linear guide.

4. The microscope of claim 1 including a driver arranged to position the carrier member under computer control.

5. A scanning microscope having an objective lens with a restricted field of view about an optical axis for examination of a portion of an object lying at the optical axis, including a tiltable focusing member defining a support plane for the object, the focusing member being mounted to rotate about a pre-established hinge axis to position said portion of the object at a focal plane of the microscope, the hinge axis lying in a plane substantially normal to the optical axis at a distance spaced therefrom sufficient that rotation of the portion of the object at the optical axis sufficiently approximates translation along the optical axis to enable focusing, a drive mechanism for rotating the focusing member about the hinge axis effective to bring into focus said portion of the object, and a mechanism for rotating the plane about the second hinge an axis orthogonal to the optical axis and the hinge axis so that the object can be scanned on a line substantially in a direction parallel to the hinge axis, a drive mechanism to produce relative oscillating scanning motion between the object and the objective lens in a direction transverse to the radial direction of the tiltable member, and, a photosensitive detector for detecting the stream of single picture elements collected produced by the objective lens, the microscope constructed and arranged to scan in a direction transverse to the radial direction of the tiltable focusing member and a laterally movable carrier mounted on the tiltable member, the carrier arranged to advance the object, relative to the optical axis, in motion in the direction of the radius of the tiltable member.

6. The microscope of claim 5 in which the scanning microscope comprises a moving objective microscope.

7. The microscope of claim 6 in which the microscope includes a flying micro-objective lens.

8. The microscope of claim 6 in which the moving objective is supported upon an oscillating rotary arm that describes an arc generally centered on a radial axis of the tiltable member.

9. The microscope of claim 5 in which the depth of field of the microscope is between about 30 and 200 micron, and the drive mechanism is a driver located outwardly along the tiltable member more distant from the hinge than the position in which the optical axis of the microscope intersects the tiltable member.

10. The microscope of claim 9 in which the distance of the driver from the. hinge axis is greater than about twice the distance of the optical axis from the hinge axis.

11. A method of microscopic examination comprising providing a microscope having an objective lens with a restricted field of view about an optical axis for examination of a portion of an object lying at the optical axis, the microscope including a tiltable focusing member defining a support plane for the object, the focusing member being mounted to rotate about a preestablished hinge axis to position said portion of the object at the focal plane of the microscope, the hinge axis lying in a plane substantially normal to the optical axis at a distance spaced therefrom sufficient that rotation of the portion of the object sufficiently approximates translation along the optical axis to enable focusing, a drive mechanism for rotating the member about the hinge axis effective to bring into focus said portion of the object, and a mechanism for rotating the plane about an axis orthogonal to the optical axis and the hinge axis, enabling the object to be scanned substantially in a direction parallel to the hinge axis, advancing the scanned object by a laterally movable carrier located above said tiltable focusing member, and under control of an automated control system, moving the movable member to bring the portion of the object into the plane of focus of the microscope.

12. The method of claim 11 in which the object comprises biological material.

13. The method of claim 11 in which the object fluoresces and the microscope is constructed to detect such fluorescence.

14. The method of claim 13 in which the object comprises an ordered array of nucleotides that may fluoresce.

15. The method of claim 13 in which the object comprises an ordered array of oligonucleotides.

16. The method of claim 13 in which the object comprises an ordered array of deposits of nucleic acid fragments.

17. The scanning microscope of claim 5 or 7 in which the scanning drive mechanism is a limited rotation oscillating motor operating at a substantial frequency.

18. A scanning microscope system including a translation and focusing device, comprising:

a scanning microscope including a scanning structure constructed to support and displace an objective lens over a plurality of locations;

a support structure constructed to receive an object for scanning by said objective lens of said scanning microscope, said support structure being constructed to rotate said object with respect to a fixed hinge axis;

a drive mechanism including a movable member constructed and arranged to displace said object about said fixed hinge axis thereby placing into focus an area of said object with respect to said objective lens of said scanning microscope; and a linear guide constructed and arranged for relative linear displacement of said support structure and said objective lens.

19. The scanning microscope of claim 18 wherein said support structure is constructed so that said fixed hinge axis is oriented perpendicularly with respect to said linear guide.

20. The scanning microscope of claim 18 wherein said scanning structure includes an oscillating rotary arm constructed lo displace said objective lens over an arc.

21. The scanning microscope of claim 18 wherein said objective lens has resolution of less than about 10 micron.

22. The scanning microscope of claim 18 including a controller constructed to perform dynamic focussing by varying a position of said drive mechanism during scanning.

23. The scanning microscope of claim 18 wherein said support structure is constructed to received said object located on a microscope slide.

24. The scanning miscoscope of claim 18 wherein said support structure is constructed to received said object located on a biochip.

25. The scanning microscope of claim 23 or 24 in which the object comprises biological material.

26. The scanning microscope of claim 23 or 24 wherein the object fluoresces and said scanning microscope is constructed to detect such fluorescence.

27. The scanning microscope of claim 23 or 24 wherein the object comprises an ordered array of nucleotides that may fluoresce.

28. The scanning microscope of claim 23 or 24 wherein the object comprises an ordered array of oligonucleotides.

29. The scanning microscope of claim 23 or 24 wherein the object comprises an ordered array of deposits of nucleic acid fragments.

30. A scanning microscope system including a translation and focusing device, comprising:

a scanning microscope including a scanning structure constructed to support and displace an objective lens over a plurality of locations;

a support structure constructed to receive an object for scanning by said objective lens of said scanning microscope, said support structure being constructed to rotate said object about a first fixed hinge axis and a second fixed hinge axis;

a drive mechanism including a first and a second movable member, said first movable member being constructed and arranged to displace said object about said first fixed hinge axis and said second movable member being constructed and arranged to displace said object about said second fixed hinge axis thereby bringing into focus an area of said object with respect to said objective lens of said scanning microscope; and a linear guide constructed and arranged for relative linear displacement of said support structure and said objective lens.

31. The scanning microscope of claim 30 wherein said support structure is constructed so that said fixed hinge axis is oriented perpendicularly with respect to said linear guide.

32. The scanning microscope of claim 30 wherein said scanning structure includes an oscillating rotary arm constructed to displace said objective lens over an arc.

33. The scanning microscope of claim 30 in which said objective lens has resolution of less than about 10 micron.

34. The scanning microscope of claim 30 including a controller constructed to perform dynamic focussing by varying a position of said drive mechanism during scanning.

35. The scanning microscope of claim 30 wherein said support structure is constructed to received said object located on a microscope slide.

36. The scanning miscoscope of claim 30 wherein said support structure is constructed to received said object located on a biochip.

37. The scanning microscope of claim 35 or 36 wherein the object comprises biological material.

38. The scanning microscope of claim 35 or 36 wherein the object fluoresces and said scanning microscope is constructed to detect such fluorescence.

39. The scanning microscope of claim 35 or 36 wherein the object comprises an ordered array of nucleotides that may fluoresce.

40. The scanning microscope of claim 35 or 36 wherein the object comprises an ordered array of oligonucleotides.

41. The scanning microscope of claim 35 or 36 wherein the object comprises an ordered array of deposits of nucleic acid fragments.

\* \* \* \* \*

UNITED STATES PATENT AND TRADEMARK OFFICE
CERTIFICATE OF CORRECTION

PATENT NO. : 6,407,858 B1
DATED : June 18, 2002
INVENTOR(S) : Jean I. Montagu

It is certified that error appears in the above-identified patent and that said Letters Patent is hereby corrected as shown below:

<u>Title page,</u>
Item [63], Related U.S. Application Data, after "Pat. No. 6,269,846" please enter --, and a continuation-in-part of PCT/US99/00730, filed on January 13, 1999 --

Signed and Sealed this

Fifth Day of August, 2003

JAMES E. ROGAN
*Director of the United States Patent and Trademark Office*